(12) United States Patent
Toida et al.

(10) Patent No.: US 7,450,242 B2
(45) Date of Patent: Nov. 11, 2008

(54) OPTICAL TOMOGRAPHY APPARATUS

(75) Inventors: Masahiro Toida, Kanagawa-ken (JP); Yoshikatsu Morishima, Kanagawa-ken (JP); Kazuhiro Tsujita, Tokyo (JP); Hiroshi Fujita, Saitama (JP)

(73) Assignees: Fujifilm Corporation, Tokyo (JP); Fujinon Corporation, Saitama (JP)

( * ) Notice: Subject to any disclaimer, the term of this patent is extended or adjusted under 35 U.S.C. 154(b) by 80 days.

(21) Appl. No.: 11/535,361

(22) Filed: Sep. 26, 2006

(65) Prior Publication Data

US 2007/0019208 A1      Jan. 25, 2007

Related U.S. Application Data

(63) Continuation-in-part of application No. 11/389,331, filed on Mar. 27, 2006, now abandoned, and a continuation-in-part of application No. 11/298,626, filed on Dec. 12, 2005, now abandoned, and a continuation-in-part of application No. 11/298,478, filed on Dec. 12, 2005, now abandoned.

(30) Foreign Application Priority Data

| Dec. 10, 2004 | (JP) | ............................. | 2004-358442 |
| Mar. 25, 2005 | (JP) | ............................. | 2005-089992 |
| Mar. 25, 2005 | (JP) | ............................. | 2005-089993 |
| Jun. 6, 2005 | (JP) | ............................. | 2005-165734 |
| Dec. 7, 2005 | (JP) | ............................. | 2005-353158 |
| Dec. 7, 2005 | (JP) | ............................. | 2005-353161 |
| Mar. 23, 2006 | (JP) | ............................. | 2006-079933 |
| Jun. 9, 2006 | (JP) | ............................. | 2006-161045 |

(51) Int. Cl.
*G01B 9/02*        (2006.01)

(52) U.S. Cl. .................................................... 356/479

(58) Field of Classification Search ................. 356/477, 356/479, 484, 497; 250/227.19, 227.27; 385/12
See application file for complete search history.

(56) References Cited

U.S. PATENT DOCUMENTS 5,329,134 A        7/1994    Morrison et al.

(Continued)

FOREIGN PATENT DOCUMENTS

DE         198 53 669 A1        5/1999

(Continued)

OTHER PUBLICATIONS

European Search Report dated Nov. 13, 2006 issued in European Application No. 06 00 6317.

(Continued)

*Primary Examiner*—Michael A Lyons
(74) *Attorney, Agent, or Firm*—Sughrue Mion, PLLC

(57) ABSTRACT

Low coherence light having a central wavelength $\lambda c$ of 1.1 μm and a full width at half maximum spectrum $\Delta\lambda$ of 90 nm is emitted. The low coherence light has wavelength properties suited for the light absorbing properties, the diffusion properties, and the dispersion properties of living tissue. A light dividing means divides the low coherence light into a measuring light beam, which is irradiated onto a measurement target via an optical probe, and a reference light beam that propagates toward an optical path length adjusting means. A multiplexing means multiplexes a reflected light beam, which is the measuring light beam reflected at a predetermined depth of the measurement target, and the reference light beam, to form coherent light. A coherent light detecting means detects the optical intensity of the multiplexed coherent light. An image obtaining means performs image processes, and displays an optical tomographic image on a display apparatus.

17 Claims, 17 Drawing Sheets

U.S. PATENT DOCUMENTS

| | | | |
|---|---|---|---|
| 5,874,803 A | 2/1999 | Carbuzov et al. | |
| 6,069,698 A * | 5/2000 | Ozawa et al. | 356/511 |
| 6,377,349 B1 | 4/2002 | Fercher | |
| 6,728,571 B1 | 4/2004 | Barbato | |
| 7,119,324 B2 * | 10/2006 | Voigt | 250/227.14 |
| 7,133,137 B2 * | 11/2006 | Shimmick | 356/497 |
| 2002/0196446 A1 | 12/2002 | Jonathan et al. | |
| 2003/0055342 A1 | 3/2003 | Toida | |
| 2004/0109164 A1 * | 6/2004 | Horii et al. | 356/479 |
| 2005/0265405 A1 | 12/2005 | Mannstadt et al. | |
| 2007/0076213 A1 | 4/2007 | Kato | |
| 2007/0077095 A1 | 4/2007 | Kato | |

FOREIGN PATENT DOCUMENTS

| | | | |
|---|---|---|---|
| JP | 6165784 A | 6/1994 | |
| JP | 2003-139688 A | 5/2003 | |
| WO | WO 00/19889 A1 | 4/2000 | |
| WO | WO 01/50955 A1 | 7/2001 | |

OTHER PUBLICATIONS

Yun et al. "Pulsed-source and swept-source spectral-domain optical coherence tomography with reduced motion artifacts", Optics Express. vol. 12. No. 23. Nov. 15, 2004. pp. 5614-5624.

Das et al. "Time-resolved fluorescence and photon migration studies in biomedical and model random media". Rep. Prog. Phys. vol. 60. 1997. pp. 227-232.

"ss-225". Micron Optics. 2003. retrieved from Internet.

"SLD-53-MP". Superlum Diodes. Ltd., Feb. 3, 2006. retrieved from Internet.

"Axiable Actloesung OC'1'".Medoet Gruppe. Univ. Wien. Austria. 2005. retrieved from Internet.

Shidlovski V et al., "Superluminescent diodes for optical coherence tomography", Proceedings of the SPIE—The International Society for Optical Engineering SPIE—Int. Soc. Opt. Eng USA, vol. 4648, 2002 pp. 139-147, XP002372505 ISSN: 0277-786X.

Bizheva K K et al., "High resolution spectroscopic optical coherence tomography in the 900-1100 nm wavelength range", Proceedings of the SPIE—The International Society for Optical Engineering SPIE—Int. Soc. Opt. Eng USA, vol. 4619, pp. 249-252, XP002372506 ISSN: 0277-786x.

I Hartl et al., "Ultrahigh-resolution optical coherence tomography using continuum generation in air-silica microstructure optical fiber", Optics Letters, vol. 26, No. 9, May 1, 2001, pp. 608-610.

Wang et al., "Optimal wavelength for ultrahigh-resolution optical coherence tomography", Optics Express, vol. 11, No. 12, Jun. 16, 2003, 7 pages.

Drexler et al., "In vivo ultrahigh-resolution optical coherence tomography", Optics Letters, vol. 24, No. 17, Sep. 1, 1999, pp. 1221-1223.

* cited by examiner

PRIOR ART

OPTICAL TOMOGRAPHY APPARATUS

This is a Continuation-In-Part of application Ser. Nos. 11/298,478 filed Dec. 12, 2005, 11/298,626 filed Dec. 12, 2005, and 11/389,331 filed Mar. 27, 2006. The entire disclosures of the prior applications, application Ser. Nos. 11/298,478; 11/298,626 and 11/389,331 are hereby incorporated by reference.

BACKGROUND OF THE INVENTION

1. Field of the Invention

The present invention relates to an optical tomography apparatus that irradiates a low coherence measuring light beam onto a measurement target to obtain tomographic images of the measurement target. Particularly, the present invention relates to an optical tomography apparatus that obtains images of the surface and the fine structures within the measurement target, based on a reflected light beam, which is the measuring light beam reflected by the measurement target.

2. Description of the Related Art

As conventional methods for obtaining tomographic images of measurement targets, such as living tissue, methods that obtain optical tomographic images by OCT (Optical Coherence Tomography) measurement have been proposed. As an example of an OCT measurement method, the TD-OCT (Time Domain Optical Coherence Tomography) measurement has been proposed (refer to Japanese Unexamined Patent Publication Nos. 6(1994)-165784 and 2003-139688). The TD-OCT measurement is a type of light interference measurement method that utilizes the fact that light interference is detected only when the optical path lengths of divided light beams, that is, a measurement light beam and a reference light beam, match within a range of coherence length of a light source. That is, in this method, a low coherent light beam emitted from a light source is divided into a measuring light beam and a reference light beam, the measuring light beam is irradiated onto a measurement target, and the measurement light beam reflected by the measurement target is led to a multiplexing means.

In the TD-OCT measurement, the measuring position (measuring depth) within the measurement target is changed, by changing the optical path length of either the reference light beam or the measuring light beam. Thereby, a one dimensional tomographic image in the direction of the optical axis is obtained. For example, the TD-OCT apparatus disclosed in Japanese Unexamined Patent Publication No. 6(1994)-165784 comprises an optical system that causes a reference light beam emitted from an optical fiber to be reflected by a mirror. The optical path length of the reference light beam is adjusted by moving the mirror in the direction of the optical axis of the reference light beam. In addition, the irradiation position of a measuring light beam, which is irradiated on a measurement target, is scanned in a direction perpendicular to the optical axis thereof, thereby enabling obtainment of two dimensional tomographic images based on two dimensional reflected optical intensities. Further, by scanning the irradiation position of the measuring light beam two dimensionally perpendicular to the optical axis thereof, three dimensional tomographic images can be obtained, based on three dimensional reflected optical intensities.

As another OCT measurement method, a method that obtains optical tomographic images by SD-OCT (Spectral Domain Optical Coherence Tomography) measurement has been proposed (refer to U.S. Pat. No. 6,377,349). In an SD-OCT apparatus, a wide band low coherence light beam is divided into a measuring light beam and a reference light beam. The optical path lengths of the measuring light beam and the reference light beam are substantially matched, then the two light beams are caused to interfere with each other, to form a coherent light beam. Thereafter, the coherent light beam is decomposed into different frequency components by a spectral decomposing means. An array type photodetector measures the intensity of each frequency component of the coherent light beam. The coherent spectral waveform obtained by the photodetector undergoes Fourier transform at a computer, to obtain one dimensional tomographic data in the direction of the optical axis, without physically changing the optical path length. By scanning the measuring light beam in directions perpendicular to the optical axis, two dimensional and three dimensional tomographic images can be obtained.

Further, the SS-OCT (Swept Source Optical Coherence Tomography) method has been proposed in U.S. Pat. No. 5,956,355. In the SS-OCT method, a coherent light beam, of which the frequency is temporally varied, is emitted instead of a low coherence light beam. The coherent light beam is detected, and reflection intensities at depth positions within a measurement target are calculated, based on interferograms of optical frequency regions. Then, tomographic images are generated employing the calculated reflection intensities.

These OCT apparatuses have been developed and are in use in the field of ophthalmology. Following the use of OCT apparatuses in the field of ophthalmology, research and development are underway for application in endoscopes. In the initial stages of development, the 0.8 μm band had been employed as the wavelength of the light sources of the OCT apparatuses (refer to W. Drexler et al., Optics Letters Vol. 24, No. 17, pp 1221-1223, 1999.). This wavelength band was selected as a result of considering absorption properties of living tissue. FIG. 1A is a graph that illustrates light absorption coefficients of water, blood, melanin, and epidermis. FIG. 1B is a graph that illustrates the absorption coefficients of water with respect to light having wavelengths between 0.7 μm and 1.6 μm. From the graph of FIG. 1B, it can be seen that the peak of absorption occurs at 0.98 μm and at 1.2 μm. In addition, the broken line in the graph of FIG. 2 is a graph that represents absorption loss in living tissue, based on the absorption coefficients. From the graph of FIG. 2, it can be seen that light within the 0.8 μm band has the smallest amount of absorption loss. For this reason, it was considered that light within the 0.8 μm band has the highest transmissivity with respect to living tissue, enables deeper measurement depths, and is most suited for OCT apparatuses.

However, it has been found recently that scattering properties also limit measurement depths in OCT apparatuses. This is because OCT apparatuses detect backscattered reflected light beams from within living tissue. Rayleigh scattering is common within living tissue. In Rayleigh scattering, the scattering intensity is inversely proportionate to wavelength to the fourth power. The dotted line in the graph of FIG. 2 represents scattering loss within living tissue. The total loss, represented by the solid line in the graph of FIG. 2, is the sum of the absorption loss and the scattering loss.

From the graph of FIG. 2, it can be seen that the wavelength band, at which total loss is minimal, is the 1.3 μm band. For this reason, after OCT apparatuses for ophthalmology were realized, research and development for OCT apparatuses to be applied to endoscopes, which require deeper imaging depths, are being performed with the 1.3 μm band as the wavelength of light sources therein (refer to Japanese Unexamined Patent Publication No. 2003-139688).

The purpose for applying an OCT apparatus to an endoscope is to enable definitive diagnoses within living organisms, and to diagnose the depth of tumor invasion of mucosal cancer (m cancer) and submucosal cancer (sm cancer). Hereinafter, the procedure of endoscopic diagnosis of cancer will be briefly described. First, a diseased portion is discovered within a normal observation image, and whether the disease is cancer or another illness is discriminated. This preliminary diagnosis is based on the experience of a physician, after which tissue from a portion estimated to be cancerous is collected and subjected to a biopsy, to obtain a definitive diagnosis. For this reason, it is presently difficult to obtain definitive diagnoses during examination with an endoscope. In the case that a diseased portion is definitively diagnosed as cancer, the depth of tumor invasion is diagnosed by endoscopic examination, in order to determine a treatment strategy. Commonly, cancers present themselves in the mucoepidermis, and metastasize in the horizontal direction and in the depth direction, as the disease progresses. As illustrated in FIG. 3, the structure of a stomach wall is constituted by: a membrana mucosa (m) layer; lamina muscularis mucosae (MM); a submucosal (sm) layer; tunica muscularis ventriculi; and a serous membrane. Cancers which are present only in the membrana mucosa layer are designated as m cancers, and cancers which have penetrated to the submucosal layer are designated as sm cancers. Treatment protocols differ between m cancers and sm cancers. Blood vessels and lymph systems are present in the submucosal layer, and there is a possibility of metastasis in the case of sm cancers. Therefore, surgical procedures are required. On the other hand, there is no possibility of metastasis in the case of m cancers. Therefore, m cancers are removed by endoscopic procedures. For this reason, it is necessary to discriminate whether cancers are m cancers or sm cancers. Specifically, it is important to be able to evaluate whether the layer structure of the lamina muscularis mucosae layer is maintained or destroyed, in an image. Presently, application of ultrasound imaging techniques is being considered, with the objective of diagnosing the depth of tumor invasion. However, the resolution of ultrasound imaging is only about 100 μm in the axial direction, which is insufficient to visualize the MM layer. In addition, in m cancers which have progressed, lymph follicles are formed under the MM layer, thereby causing the cancerous portions and the lymph follicles to be imaged integrally, and m cancers may be misdiagnosed as sm cancers. For this reason, an imaging method having a resolution of 10 μm or less in the axial direction is desired, to enable accurate diagnosis of the depth of tumor invasion.

Meanwhile, the resolutions of TD-OCT and SD-OCT apparatuses in the optical axis direction are determined by the coherence length of the light sources thereof. That is, it is not generally possible to obtain resolution less than the coherence length of the light source. For this reason, a light beam having a coherence length of 10 μm or less is necessary to obtain high resolution of 10 μm or less. The coherence length Δz of low coherence light is proportionate to the square of the central frequency and inversely proportionate to the spectrum width thereof. The coherence length Δz can be expressed by the following formula:

$$\Delta z = (2ln2/\Pi) \cdot (\lambda c^2/\Delta\lambda)$$

wherein
λc: central wavelength
Δλ: spectrum width

For this reason, it is necessary to broaden the spectrum width Δλ in order to decrease the coherence length. Meanwhile, it was found that the influence of dispersion needed to be considered, if the spectrum width Δλ was broadened (refer to Y. Wang et al., Optics Express Vol. 11, No. 12, 2003, pp 1411-1417, 2003.).

In a Michaelson interferometer, as a light beam propagates through a sample, phase shift occurs, and a coherent signal waveform changes as a result. If the coherent signal waveform is designated as φ(w) and the spectrum waveform of the light source is a Gaussian distribution, autocorrelation functions can be expressed as:

$$\delta_t = \delta_{t0} \cdot \left\{ 1 + \left( \frac{d^2\varphi(w)}{dw^2} \right) \delta w^4 \right\}^{\frac{1}{2}} \quad (1)$$

$$K = \delta_t / \delta_{t0} \quad (2)$$

$$D = \frac{-w_0^2}{2\pi c} \cdot \frac{d^2\varphi(w)}{dw^2} \quad (3)$$

wherein
$\delta_t$: $1/e^{1/2}$ width of the autocorrelation function
$\delta_{t0}$: $1/e^{1/2}$ width of the autocorrelation function when D=0
$\delta_w$: $1/e^{1/2}$ width of the optical spectrum
$w_0$: central frequency of the optical spectrum
K: broadening ratio due to the influence of dispersion FIG. 4 is a graph that illustrates calculated results (represented by the solid line) of formula (3) above and actual measured values (represented by the triangles). Dispersion D is zero when the wavelength of the light beam is 1.0 μm. It can be seen from the graph of FIG. 4 that the influence of dispersion becomes greater as the wavelength becomes greater than or less than 1.0 μm.

FIG. 5 is a graph that illustrates measured values and simulation results of the relationship between the distance of propagation (depth of water) and broadening ratios, when low coherence light beams having wavelengths of 1.32 μm (spectrum width: 76 nm) and 0.94 μm (spectrum width: 75 nm) propagate through water.

In the aforementioned document, Y. Wang et al. conclude that it is preferable to employ low coherence light having a central wavelength of 1.0 μm in OCT apparatuses, in the case that the coherence length of the low coherence light beam is short.

The resolution in the optical axis direction is defined by the wavelength sweep width Δλ of the coherent light beam emitted by the light source in SS-OCT apparatuses as well. For this reason, the wavelength sweep width Δλ needs to be widened, in order to increase the resolution in the optical axis direction. However, if the wavelength sweep width Δλ is widened, it becomes necessary to consider the effects of scattering, as described above.

However, when an OCT apparatus that employs low coherence light of coherent light, of which the frequency is temporally varied, is used to obtain an optical tomographic image of an organism, there are cases in which the wavelength band of the measuring light beam includes wavelengths which are readily absorbed by living tissue. In these cases, the spectral shape of the reflected light beam changes due to the light absorption by the living tissue, and side bands or side lobes appear in the autocorrelation function, generating pseudo signals that reduce the S/N ratio of the optical tomographic image. As illustrated in FIG. 1B, peaks in the absorption coefficient of water, which is the main constituent of living tissue, occur at wavelengths of 0.98 μm and 1.2 μm.

FIGS. 6A and 6B are graphs that represent simulations of a light beam having a central wavelength of 1.0 μm, a wavelength band width of 100 nm, and a Gaussian distribution propagating through water. FIG. 6A represents the changes in spectrum shape, and FIG. 6B represents Fourier transform waveforms of each spectral waveform. Note that the solid lines represent waveforms which are not transmitted through water; the long/short dashed lines represent waveforms which have been transmitted through 2 mm of water; the long/short/short dashed lines represent waveforms which have been transmitted through 4 mm of water; and the broken lines represent waveforms which have been transmitted through 8 mm of water. It can be seen from the graphs of FIGS. 6A and 6B that in the case that a measuring light beam having a central wavelength of 1 μm and a wavelength band width of 100 nm propagates through water, influence of absorption at 0.98 μm greatly changes the spectrum shape. As a result, side bands appear in the autocorrelation waveform, pseudo signals are generated, and the quality of the optical tomographic image deteriorates.

In the aforementioned document by Y. Wang et al., it is disclosed that influence due to scattering is observed when optical tomographic images are obtained employing low coherence light having a coherence length of approximately 10 μm ($\lambda c^2/\Delta\lambda=23$). In addition, Y. Wang et al. disclose that it is preferable to set the central wavelength of low coherence light in the vicinity of 1.0 μm in cases that influence due to dispersion is observed. However, there is no disclosure regarding a central wavelength $\lambda c$ nor a wavelength band width $\Delta\lambda$ that avoids influence due to absorption at the 0.98 μm and 1.2 μm wavelengths.

SUMMARY OF THE INVENTION

The present invention has been developed in view of the aforementioned problems. It is an object of the present invention to clarify the presence of optimal wavelength properties for obtaining high resolution while taking into consideration the light absorption properties, the scattering properties, and the dispersion properties of living organisms. It is another object of the present invention to realize an optical tomography apparatus that employs low coherence light or coherent light, of which the frequency is temporary varied, having the optimal wavelength properties to obtain high resolution optical tomographic images having high image quality.

The first optical tomography apparatus of the present invention comprises:

a light source, for emitting low coherence light beam;

dividing means, for dividing the low coherence light beam into a measuring light beam and a reference light beam;

an irradiating optical system, for irradiating the measuring light beam onto a measurement target;

optical path length changing means, for changing the optical path length of one of the reference light beam and the measuring light beam;

multiplexing means, for multiplexing a reflected light beam, which is the measuring light beam reflected by the measurement target, and the reference light beam, to obtain a coherent light beam; and image obtaining means, for detecting the intensity of the reflected light beam at a plurality of depth positions of the measurement target, at which the optical path length of the reference light beam and the sum of the optical path lengths of the measuring light beam and the reflected light beam substantially match, based on the optical intensity of the multiplexed coherent light beam, and for obtaining tomographic images of the measurement target, based on the intensities at each of the depth positions;

a central wavelength $\lambda c$ and a full width at half maximum spectrum $\Delta\lambda$ of the reference light beam and the reflected light beam satisfying the following conditions:

$$\lambda c^2/\Delta\lambda \leqq 15$$

$$\lambda c+(\Delta\lambda/2)\leqq 1.2 \text{ μm}$$

$$\lambda c-(\Delta\lambda/2)\geqq 0.98 \text{ μm}.$$

The second optical tomography apparatus of the present invention comprises:

a light source, for emitting a low coherence light beam;

dividing means, for dividing the low coherence light beam into a measuring light beam and a reference light beam;

an irradiating optical system, for irradiating the measuring light beam onto a measurement target;

multiplexing means, for multiplexing a reflected light beam, which is the measuring light beam reflected by the measurement target, and the reference light beam, to obtain a coherent light beam; and image obtaining means, for calculating the intensity of the reflected light beam at a plurality of depth positions of the measurement target, based on the properties of the multiplexed coherent light beam, and for obtaining tomographic images of the measurement target, based on the intensities at each of the depth positions;

a central wavelength $\lambda c$ and a full width at half maximum spectrum $\Delta\lambda$ of the reference light beam and the reflected light beam satisfying the following conditions:

$$\lambda c^2/\Delta\lambda \leqq 15$$

$$\lambda c+(\Delta\lambda/2)\leqq 1.2 \text{ μm}$$

$$\lambda c-(\Delta\lambda/2)\geqq 0.98 \text{ μm}.$$

A configuration may be adopted, wherein:

the image obtaining means detects the intensity for each frequency of the coherent light beam; and calculates the intensity of the reflected light beam at the plurality of depth positions of the measurement target, based on the detected intensities for each frequency of the coherent light beam.

Note that here, the "reflected light beam" refers to: light which is reflected by the measurement target; light which is backscattered by the measurement target; and light which is both reflected and backscattered by the measurement target.

In addition, the reference light beam and the reflected light beam have substantially the same central wavelengths and full width at half maximum spectra. The phrase "substantially the same" refers to a degree of uniformity that does not cause adverse effects in measurement of the intensity of the coherent light beam.

The light source may comprise a super luminescent diode. The super luminescent diode may comprise: a GaAs substrate having a first conductivity; an optical waveguide path constituted by an InGaAs active layer on the GaAs substrate; and a window region layer having a greater energy gap and a smaller refractive index than the active layer and a second conductivity different from the first conductivity, constituted by a binary or ternary semiconductor material with a lattice coefficient that lattice matches with GaAs within a range of ±0.1% and does not contain Al, provided at a rear emitting facet of the optical waveguide path. The semiconductor material of the window region layer may be one of GaAs and InGaP.

The light source may comprise phosphor that contains near infrared fluorescent pigment.

The light source may comprise one of a Yb type pulse laser, an Nd type pulse laser, and a Ti type pulse laser. Note that a Yb:YAG laser, a Yb:Glass laser, or a Yb type fiber laser may be utilized as the Yb type pulse laser. An Nd:YAG laser, an Nd:Glass laser, or an ND type fiber laser may be utilized as the Nd type pulse laser.

Further, the optical tomography apparatus may comprise a Gaussian spectrum forming filter, in addition to the aforementioned structures. In this case, the central wavelength and the full width at half maximum spectrum of the low coherence light beam emitted from the light source itself may be of any values, as long as the low coherence light beam satisfies the above conditions after passing through the Gaussian spectrum forming filter.

The third optical tomography apparatus of the present invention comprises:

a light source, for emitting a laser beam while sweeping through wavelengths at a predetermined period;

dividing means, for dividing the laser beam into a measuring light beam and a reference light beam;

an irradiating optical system, for irradiating the measuring light beam onto a measurement target;

multiplexing means, for multiplexing a reflected light beam, which is the measuring light beam reflected by the measurement target, and the reference light beam, to obtain a coherent light beam;

coherent light detecting means, for calculating the intensity of the reflected light beam at a plurality of depth positions within the measurement target, based on the frequency and the intensity of the coherent light beam; and image obtaining means, for obtaining tomographic images of the measurement target, based on the intensities of the reflected light beam at each of the depth positions;

the central wavelength $\lambda c$ of the sweep and the wavelength sweep width $\Delta\lambda$ of the laser light beam satisfying the following conditions:

$\lambda c^2/\Delta\lambda \leq 15$ $\lambda c+(\Delta\lambda/2) \leq 1.2\ \mu m$ $\lambda c-(\Delta\lambda/2) \geq 0.98\ \mu m$.

Note that the coherent light detecting means may comprise an InGaAs type photodetector.

As described previously, peaks in the light absorption coefficient of water, which is the main constituent of living tissue, occur at wavelengths of 0.98 $\mu m$ and 1.2 $\mu m$. For this reason, when obtaining optical tomographic images employing highly transmissive light beams having wavelengths in the vicinity of 1.1 $\mu m$, side bands appear in the autocorrelation function due to the light absorption peaks at 0.98 $\mu m$ and 1.2 $\mu m$. The side bands generate pseudo signals that deteriorate the quality of the optical tomographic images. Accordingly, it is necessary to set the central wavelength $\lambda c$ and the full width at half maximum spectrum $\Delta\lambda$ of the reference light beam and the reflected light beam such that they do not overlap the light absorption peaks at 0.98 $\mu m$ and 1.2 $\mu m$, at least within the range of the full width at half maximum spectrum $\Delta\lambda$. Therefore, the following formulas are introduced:

$\lambda c+(\Delta\lambda/2) \leq 1.2\ \mu m$ $\lambda c-(\Delta\lambda/2) \geq 0.98\ \mu m$ That is, the first optical tomography apparatus of the present invention comprises: a light source, for emitting low coherence light beam; dividing means, for dividing the low coherence light beam into a measuring light beam and a reference light beam; an irradiating optical system, for irradiating the measuring light beam onto a measurement target; optical path length changing means, for changing the optical path length of one of the reference light beam and the measuring light beam; multiplexing means, for multiplexing a reflected light beam, which is the measuring light beam reflected by the measurement target, and the reference light beam, to obtain a coherent light beam; and image obtaining means, for detecting the intensity of the reflected light beam at a plurality of depth positions of the measurement target, at which the optical path length of the reference light beam and the sum of the optical path lengths of the measuring light beam and the reflected light beam substantially match, based on the optical intensity of the multiplexed coherent light beam, and for obtaining tomographic images of the measurement target, based on the intensities at each of the depth positions; a central wavelength $\lambda c$ and a full width at half maximum spectrum $\Delta\lambda$ of the reference light beam and the reflected light beam satisfying the conditions: $\lambda c^2/\Delta\lambda \leq 15$; $\lambda c+(\Delta\lambda/2) \leq 1.2\ \mu m$; and $\lambda c-(\Delta\lambda/2) \geq 0.98\ \mu m$. Therefore, the transmissivity of the light beam is favorable, and the influence of light absorption having its peaks at the wavelengths 0.98 $\mu m$ and 1.2 $\mu m$ is reduced. Accordingly, high resolution optical tomographic images having high image quality can be obtained. Note that FIG. 7 illustrates a graph that represents central wavelengths $\lambda c$ and full width at half maximum spectrums $\Delta\lambda$ that satisfy the above formulas.

In the case that the value of $\lambda c^2/\Delta\lambda$ is large, that is, the coherence length is long and the full width at half maximum spectrum is narrow, there is almost no influence due to dispersion by water. However, when the value of $\lambda c^2/\Delta\lambda$ is small, the influence due to dispersion by water cannot be ignored.

From the simulation results of FIG. 5, it can be seen that if the central wavelength is in the vicinity of 1.32 $\mu m$, and optical tomographic images are obtained employing low coherence light having spectrum widths $\Delta\lambda$ of approximately 76 nm, influence due to dispersion is observed. However, it is difficult to compare this case to influence due to dispersion in a case in which low coherence light having a central wavelength $\lambda c$ in the 1.1 $\mu m$ band, without considering the two parameters of central wavelength $\lambda c$ and spectrum width Therefore, the present inventor conducted experiments to compare the influence due to dispersion in cases that low coherence light having central wavelengths $\lambda c$ in the 1.3 $\mu m$ band and in the 1.1 $\mu m$ band are employed to obtain optical tomographic images, with the coherence lengths of the low coherence light, that is, $\lambda c^2/\Delta\lambda$, as parameters.

In the case of FIG. 5, in which the central wavelength $\lambda c=1.32\ \mu m$ and the spectrum width $\Delta\lambda=76$ nm, that is, $\lambda c^2/\Delta\lambda=23$, the broadening ration (degree of deterioration) was 1.03 when the light propagated through 2 mm of water, 1.15 when the light propagated through 4 mm of water, and 1.65 when the light propagated through 10 mm of water.

FIG. 8B illustrates the results of experiments to determine the degrees of deterioration of resolution in the direction of the optical axis, when light having a central wavelength $\lambda c=1.32\ \mu m$ and the spectrum width $\Delta\lambda=115$ nm, that is, $\lambda c^2/\Delta\lambda=15$, is caused to propagate through 2 mm, 4 mm, and 10 mm of water. The spectra of the low coherence light are illustrated in FIG. 8A. As illustrated in FIG. 8B, the degree of deterioration was 18.2/15.2=1.2 for 2 mm of water, 1.4 for 4 mm of water, and 1.97 for 10 mm of water. That is, the deterioration in resolution in the optical axis direction is conspicuous.

Further, the degree of deterioration in resolution in the optical axis direction was measured at $\lambda c^2/\Delta\lambda=15$, in which deterioration is conspicuous for light having a central wavelength λc=1.32 μm, with light having a central wavelength λc=1.15 μm. FIG. 8D illustrates the results of experiments to determine the degrees of deterioration of resolution in the direction of the optical axis, when light having a central wavelength λc=1.15 μm and the spectrum width Δλ=90 nm, that is, $\lambda c^2/\Delta\lambda = 14.7$, is caused to propagate through 2 mm, 4 mm, and 10 mm of water. The spectra of the low coherence light are illustrated in FIG. 8C. As illustrated in FIG. 8D, the degree of deterioration was 1 for 2 mm of water, 1 for 4 mm of water, and 1.14 for 10 mm of water. That is, deterioration in resolution in the optical axis direction did not occur in this case.

From the above experimental results, it was determined that in the range of $\lambda c^2/\Delta\lambda \leq 15$, deterioration in resolution occurs conspicuously with central wavelengths λc in the 1.32 μm band, but that deterioration does not occur with central wavelengths λc in the 1.1 μm band. From these results, the range, in which light beams having central wavelengths in the 1.0 μm band are superior to those having central wavelengths in the 1.3 μm band can be defined as:

$$\lambda c^2/\Delta\lambda \leq 15.$$

By employing a super luminescent diode as the light source for the optical tomography apparatus, a low-cost and easily handled apparatus can be realized. The present inventors focused on a super luminescent diode having a window structure at an end facet of an optical waveguide path as the light source for the optical tomography apparatus. Development of the super luminescent diode was initiated, but desirable element life was not obtainable with conventionally known structures for super luminescent diodes. Through experimentation, the present inventors discovered that there are important conditions other than the material of the window region layer that need to be considered.

First, consider a case that an InGaAs active layer is employed to obtain a light beam having a central wavelength greater than or equal to 0.98 μm and less than 1.2 μm. InGaAs deteriorates at temperatures of 650° and greater. Therefore, it is preferable that processing steps following forming of the active layer be performed within an atmosphere of 650° or less. AlGaAs is frequently utilized as the material for windows, in super luminescent diodes having window structures as described above. However, it is known that it is preferable to form semiconductor layers containing Al at high temperatures. This is because oxygen is incorporated into the material when the atmospheric temperature is low (refer to F. Bugge et al., J. Crystal Growth Vol. 272 (2004) pp. 531-537).

In experiments, window region layers were produced with materials that contain Al, for example, AlGaAs, at temperatures less than or equal to 650°. In these cases, oxygen was incorporated into the window region layer, thereby increasing non-light emitting recombined centers. The increased non-light emitting recombined centers generate heat, thereby causing it to be difficult to obtain a desired element life.

Generally, active layers are approximately 100 Å thick, whereas it is necessary to grow films at least several hundreds of nm, to form window region layers. In experiments, films for window region layers were formed on a GaAs substrate, from materials that do not lattice match with GaAs. It was learned that in these cases, the crystal film quality deteriorated, thereby causing it to be difficult to obtain a desired element life. For example, consider a case in which InGaAs, which has less In than InGaAs that forms the active layer, is employed to form the window region layer. In this case, the InGaAs does not lattice match with the GaAs substrate. Therefore, an InGaAs layer having favorable crystal film quality cannot be formed, thereby causing it to be difficult to obtain a desired element life.

InGaAsP is a material that lattice matches with the GaAs substrate, and has a greater energy gap than the InGaAs active layer. However, it was learned in experiments that if such quaternary semiconductor materials are employed as the material for a layer, such as a window region layer, which is stacked on various crystal surfaces, the ratio of the four materials becomes unbalanced, deteriorating the crystal film quality. In addition, if the crystal is grown at atmospheric temperatures less than or equal to 650°, hillocks are generated and crystal film quality deteriorates, thereby decreasing the reliability of the element.

Accordingly, a super luminescent diode comprising: a GaAs substrate having a first conductivity; an optical waveguide path constituted by an InGaAs active layer on the GaAs substrate; and a window region layer having a greater energy gap and a smaller refractive index than the active layer and a second conductivity different from the first conductivity, constituted by a binary or ternary semiconductor material with a lattice coefficient that lattice matches with GaAs within a range of ±0.1% and does not contain Al, provided at a rear emitting facet of the optical waveguide path, is employed. The binary or ternary semiconductor material is one of GaAs and InGaP. By employing such a super luminescent diode, a low coherence light beam having an undistorted sectional beam shape can be emitted easily and at low cost. In addition, by employing a light source comprising such a super luminescent diode, the reliability of the light source is improved, and as a result, the reliability of the optical tomography apparatus is also improved.

The light source may comprise phosphor that contains near infrared fluorescent pigment. In this case, a low coherence light beam having a desired wavelength band can be employed.

The light source may comprise one of a Yb type pulse laser, an Nd type pulse laser, and a Ti type pulse laser. In this case, a high output low coherence light beam can easily be employed.

Further, the light source may comprise a Gaussian spectrum forming filter. In this case, the low coherence light beam emitted from the light source itself may have any central wavelength and any full width at half maximum spectrum, thereby increasing the options for the light source. In addition, the spectrum shape of the low coherence light beam will be of a Gaussian distribution after passing through the Gaussian spectrum forming filter, and higher quality optical tomographic images can be obtained.

The second optical tomography apparatus of the present invention comprises: a light source, for emitting low coherence light beam having; dividing means, for dividing the low coherence light beam into a measuring light beam and a reference light beam; an irradiating optical system, for irradiating the measuring light beam onto a measurement target; multiplexing means, for multiplexing a reflected light beam, which is the measuring light beam reflected by the measurement target, and the reference light beam, to obtain a coherent light beam; and image obtaining means, for calculating the intensity of the reflected light beam at a plurality of depth positions of the measurement target, based on the properties of the multiplexed coherent light beam, and for obtaining tomographic images of the measurement target, based on the intensities at each of the depth positions; a central wavelength λc and a full width at half maximum spectrum Δλ of the reference light beam and the reflected light beam satisfying the conditions: $\lambda c^2/\Delta\lambda \leq 15$; $\lambda c+(\Delta\lambda/2) \leq 1.2$ μm; and λc−

($\Delta\lambda/2$)≧0.98 μm. Therefore, the transmissivity of the light beam is favorable, and the influence of light absorption having its peaks at the wavelengths 0.98 μm and 1.2 μm is reduced. Accordingly, high resolution optical tomographic images having high image quality can be obtained. In addition, in the range of $\lambda c^2/\Delta\lambda$≦15, deterioration in resolution occurs conspicuously with central wavelengths c in the 1.32 μm band, but deterioration does not occur with central wavelengths λc in the 1.1 μm band. Therefore, light beams having central wavelengths in the 1.0 μm band are particularly superior to those having central wavelengths in the 1.3 μm band.

The third optical tomography apparatus of the present invention comprises: a light source, for emitting a laser beam while sweeping through wavelengths at a predetermined period; dividing means, for dividing the laser beam into a measuring light beam and a reference light beam; an irradiating optical system, for irradiating the measuring light beam onto a measurement target; multiplexing means, for multiplexing a reflected light beam, which is the measuring light beam reflected by the measurement target, and the reference light beam, to obtain a coherent light beam; coherent light detecting means, for calculating the intensity of the reflected light beam at a plurality of depth positions within the measurement target, based on the frequency and the intensity of the coherent light beam; and image obtaining means, for obtaining tomographic images of the measurement target, based on the intensities of the reflected light beam at each of the depth positions. The central wavelength λc of the sweep and the wavelength sweep width Δλ of the laser light beam satisfies the following conditions: $\lambda c^2/\Delta\lambda$≦15; λc+($\Delta\lambda/2$)≦1.2 μm; and λc−($\Delta\lambda/2$)≧0.98 μm. Therefore, the transmissivity of the light beam is favorable, and the influence of light absorption having its peaks at the wavelengths 0.98 μm and 1.2 μm is reduced. Accordingly, high resolution optical tomographic images having high image quality can be obtained. In the case that the value of $\lambda c^2/\Delta\lambda$ is large, that is, the measurement resolution is low and the wavelength sweep width Δλ is narrow, there is almost no influence due to dispersion by water. In addition, in the range of $\lambda c^2/\Delta\lambda$≦15, deterioration in resolution occurs conspicuously with central wavelengths λc in the 1.32 μm band, but deterioration does not occur with central wavelengths λc in the 1.1 μm band. Therefore, light beams having central wavelengths in the 1.0 μm band are particularly superior to those having central wavelengths in the 1.3 μm band.

DESCRIPTION OF THE PREFERRED EMBODIMENTS

Figure 1A:
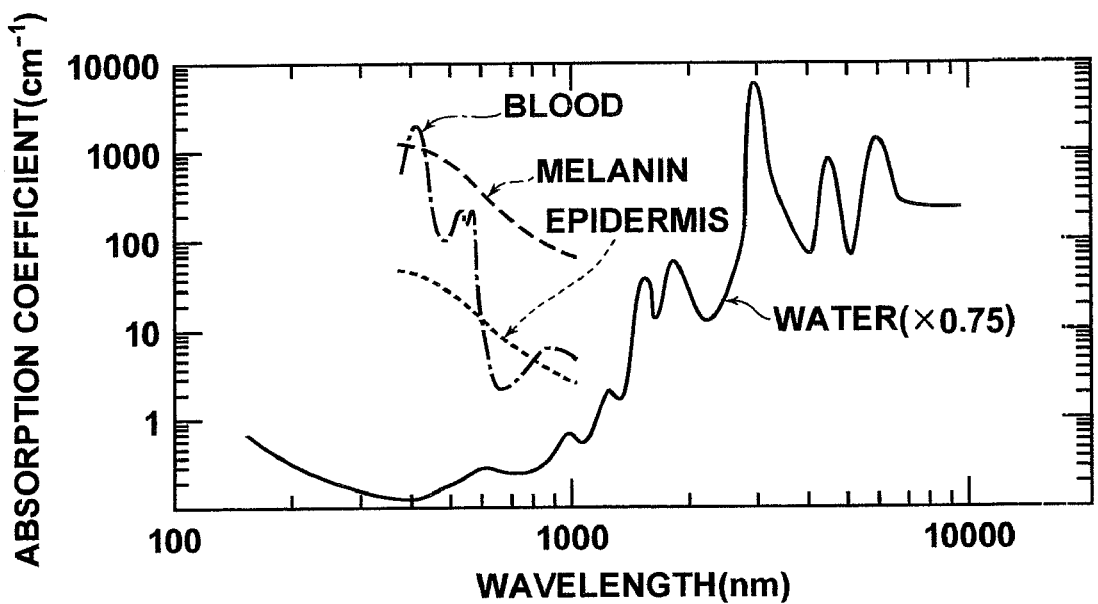
FIG. 1A is a graph that illustrates light absorption coefficients of water, blood, melanin, and epidermis.
Figure 1B:
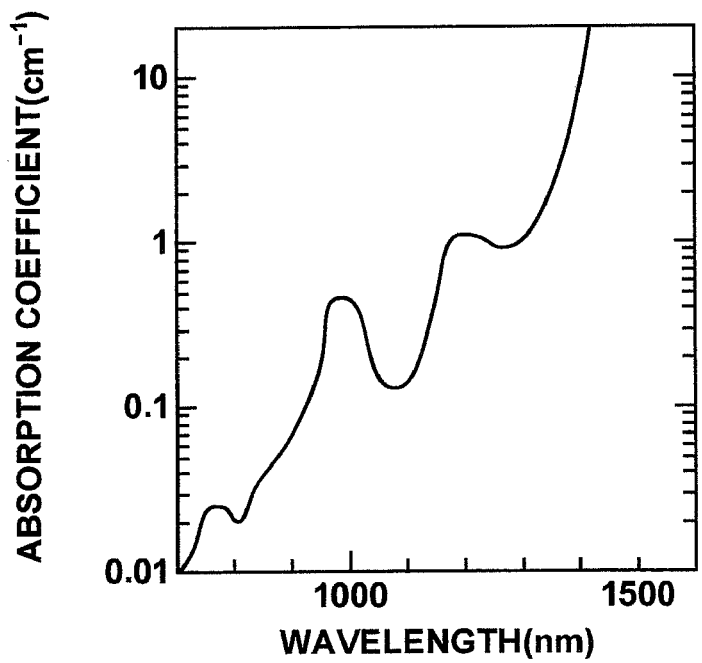
FIG. 1B is a graph that illustrates the absorption coefficients of water with respect to light having wavelengths between 0.7 μm and 1.6 μm.
Figure 2:
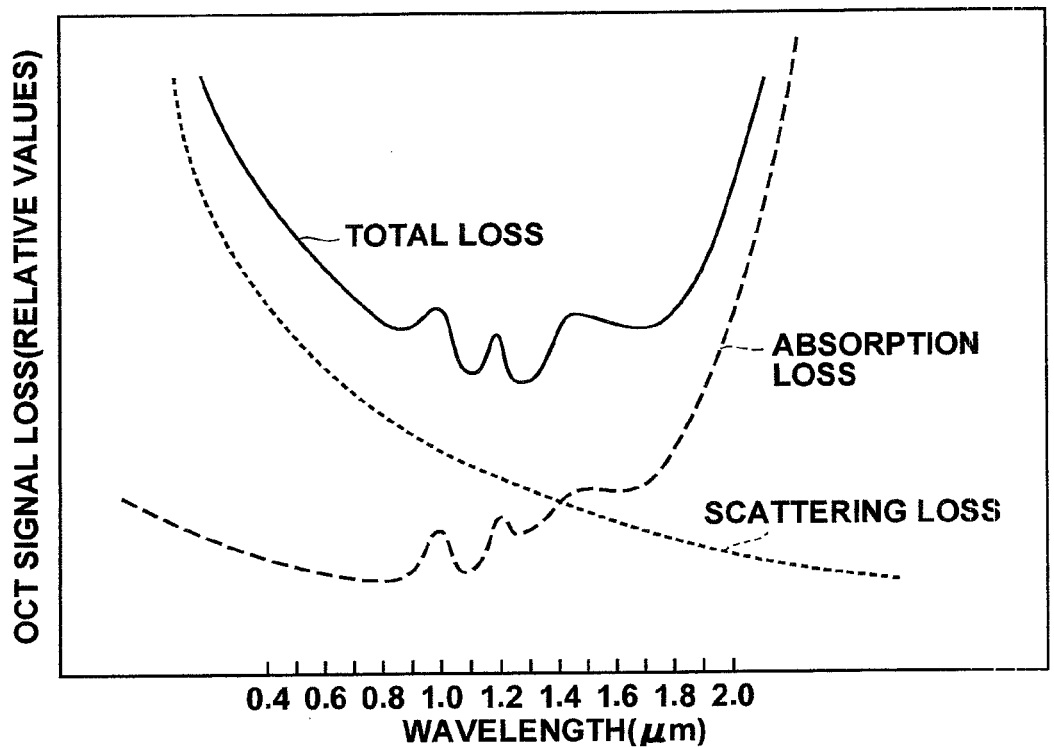
FIG. 2 is a graph for explaining absorption loss in living tissue, based on absorption coefficients.
Figure 3:
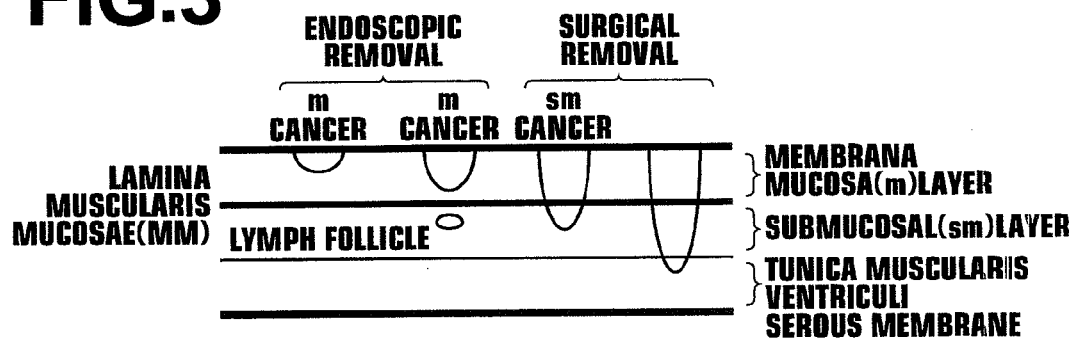
FIG. 3 is a diagram for explaining the progression of cancer in a stomach wall.
Figure 4:
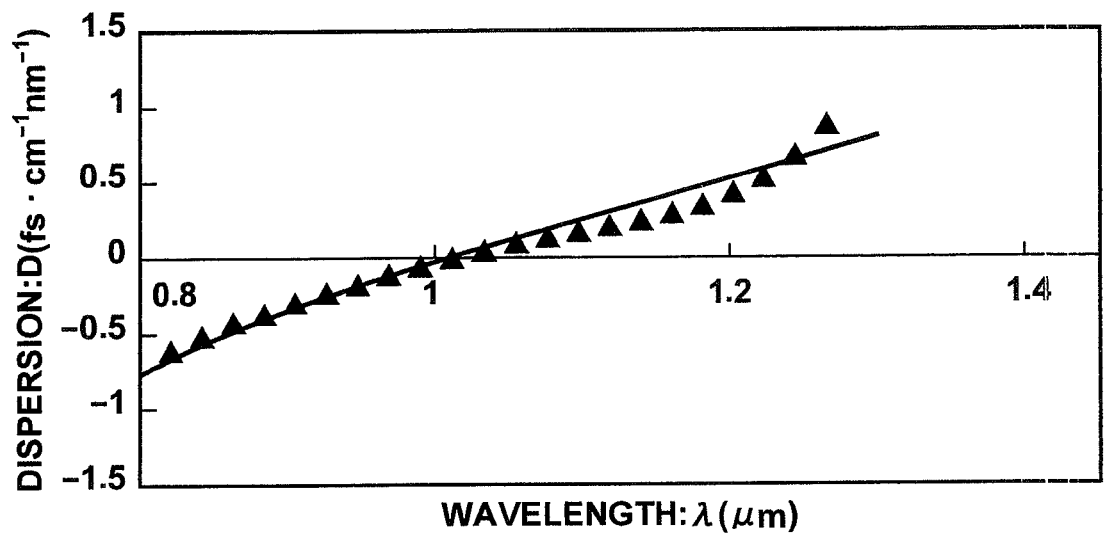
FIG. 4 is a graph for explaining dispersion properties of water.
Figure 5:
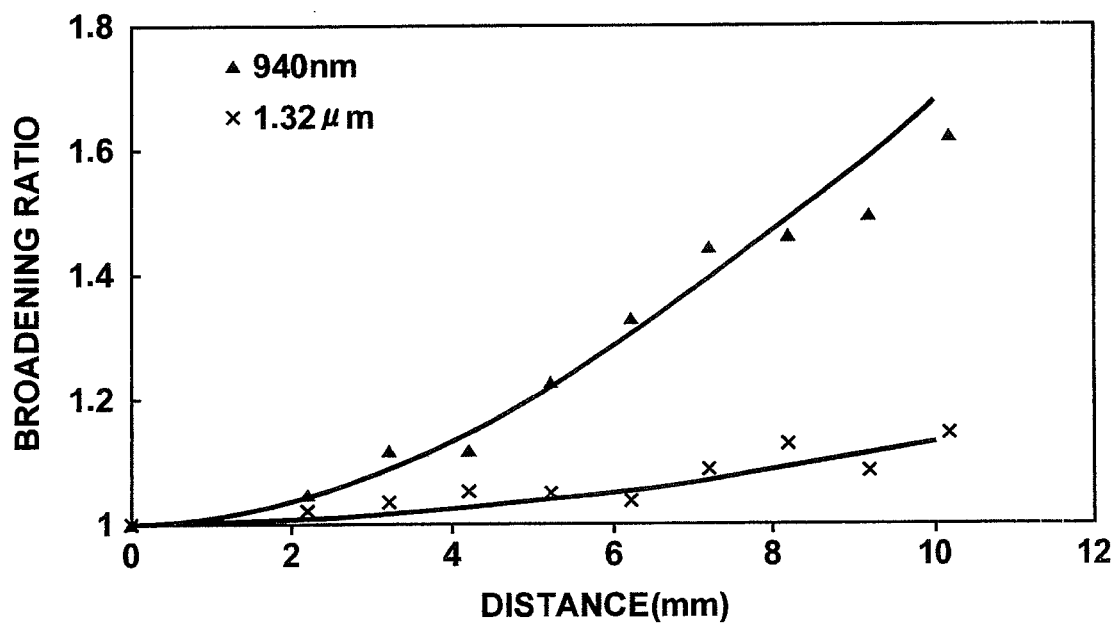
FIG. 5 is a graph for explaining the relationship between distances of propagation in water and broadening ratios.
Figure 6A:
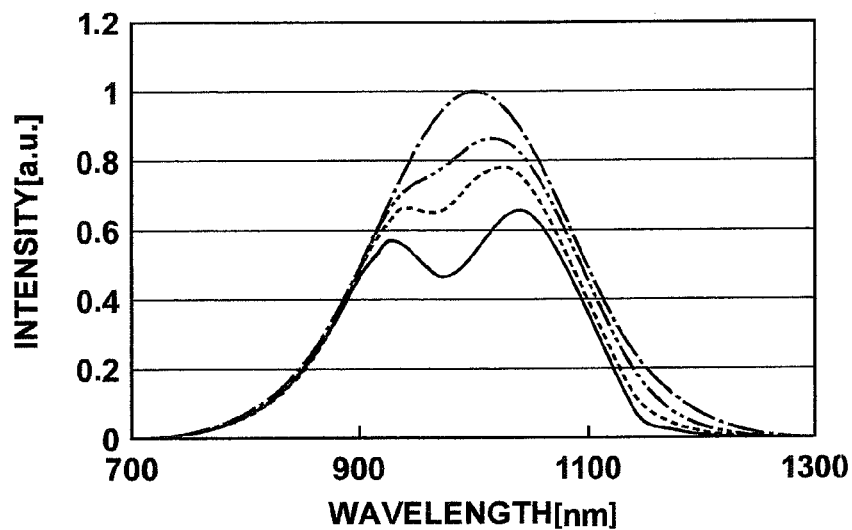
FIGS. 6A and 6B are graphs for explaining spectral waveforms and Fourier transforms thereof, respectively.
Figure 6B:
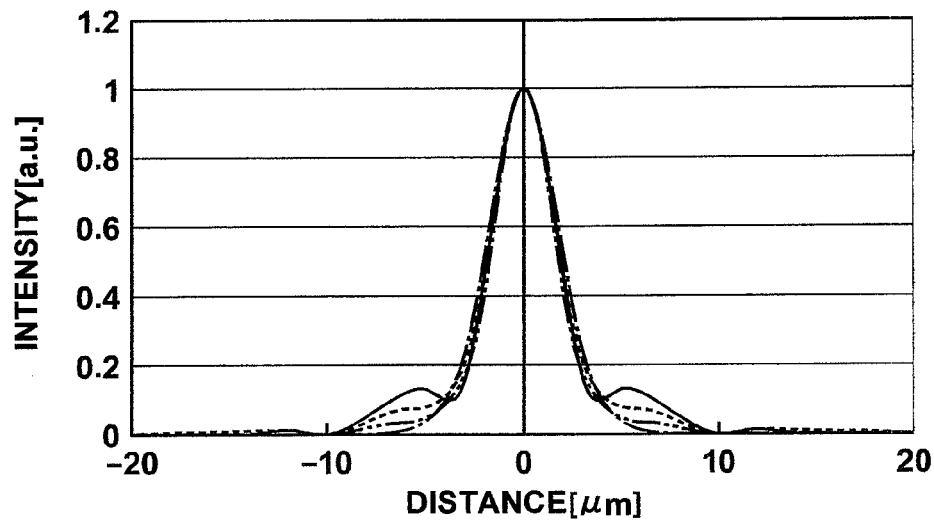
Figure 7:
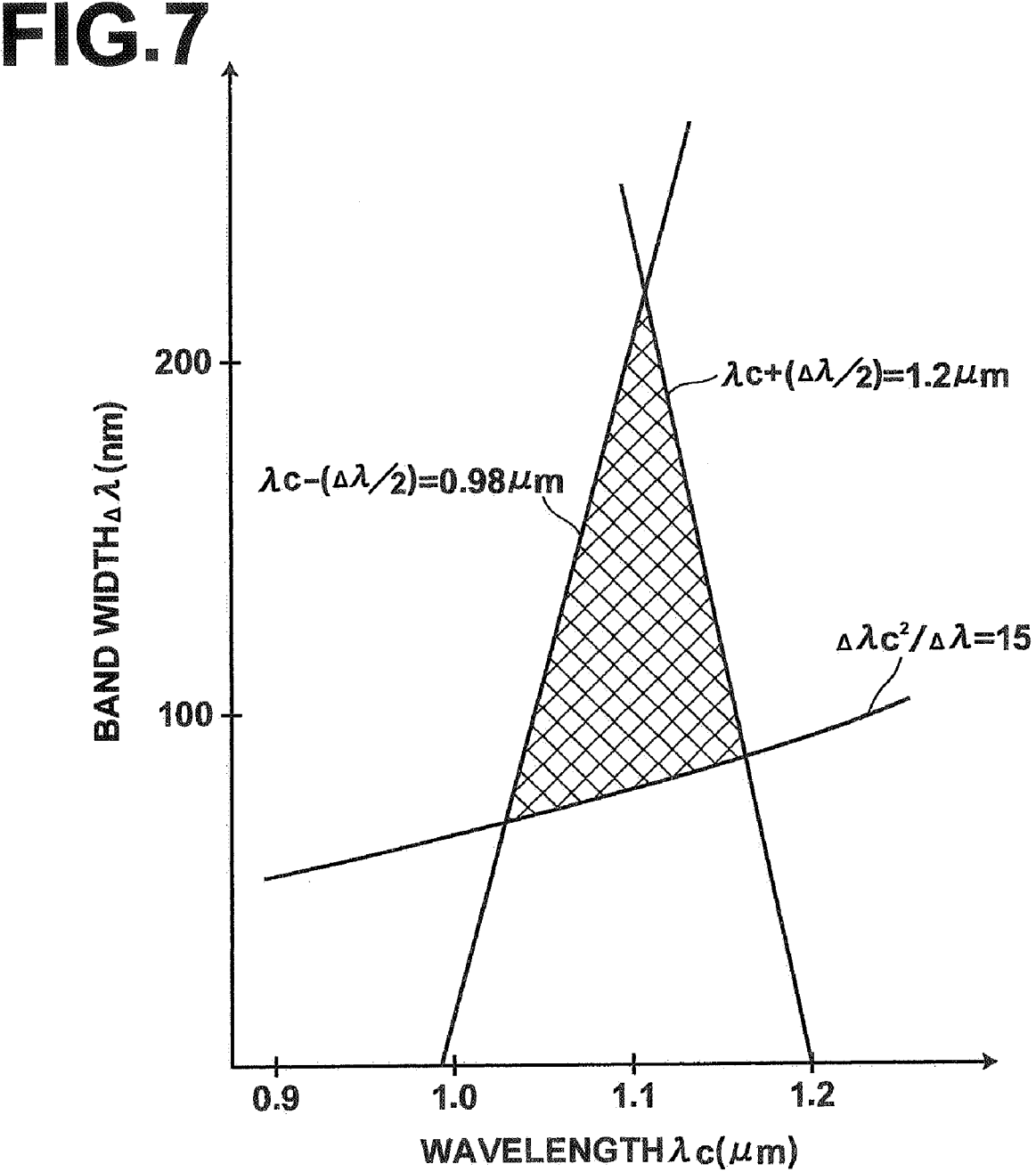
FIG. 7 is a graph for explaining the relationship between central wavelengths and spectral bandwidths.
Figure 8A:
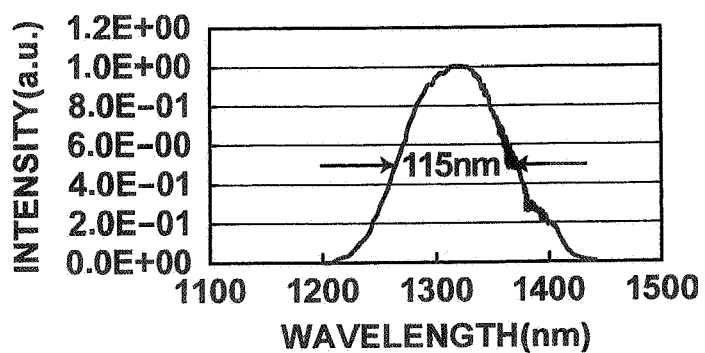
FIGS. 8A, 8B, 8C and 8D are graphs for explaining the relationships between distance propagated through water and resolution in the optical axis direction.
Figure 8B:
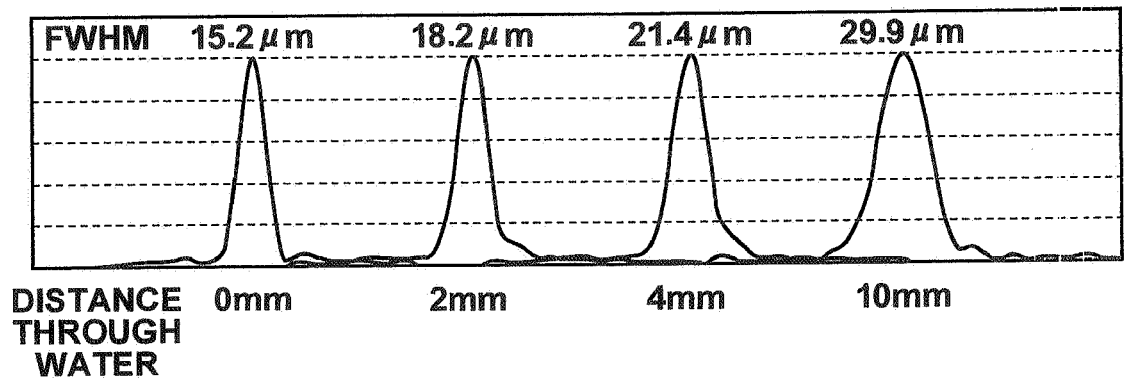
Figure 8C:
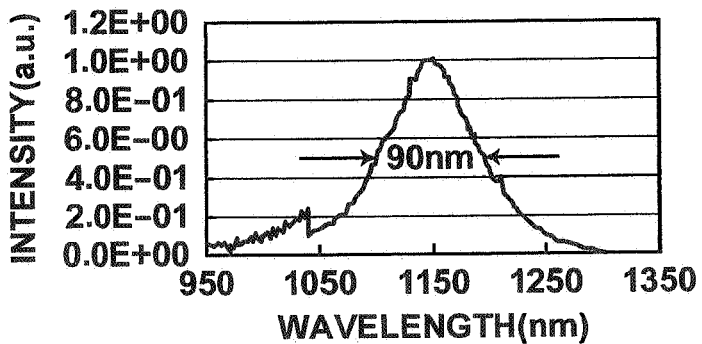
Figure 8D:
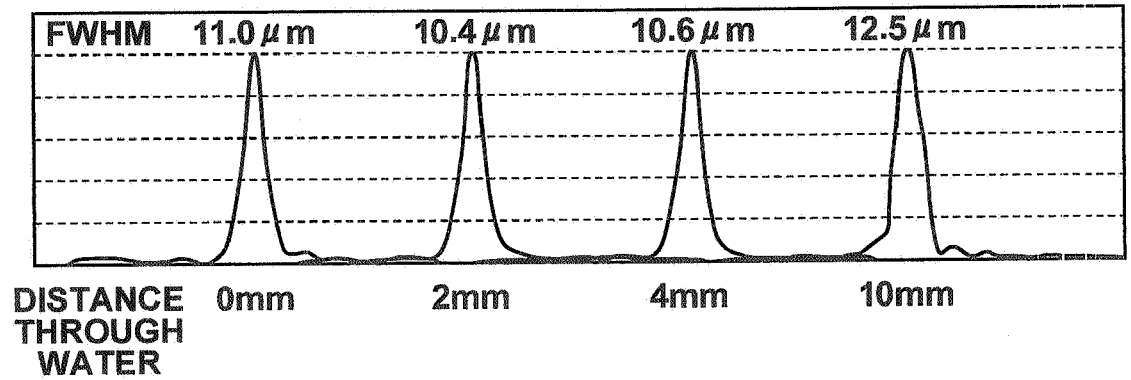
Figure 9:
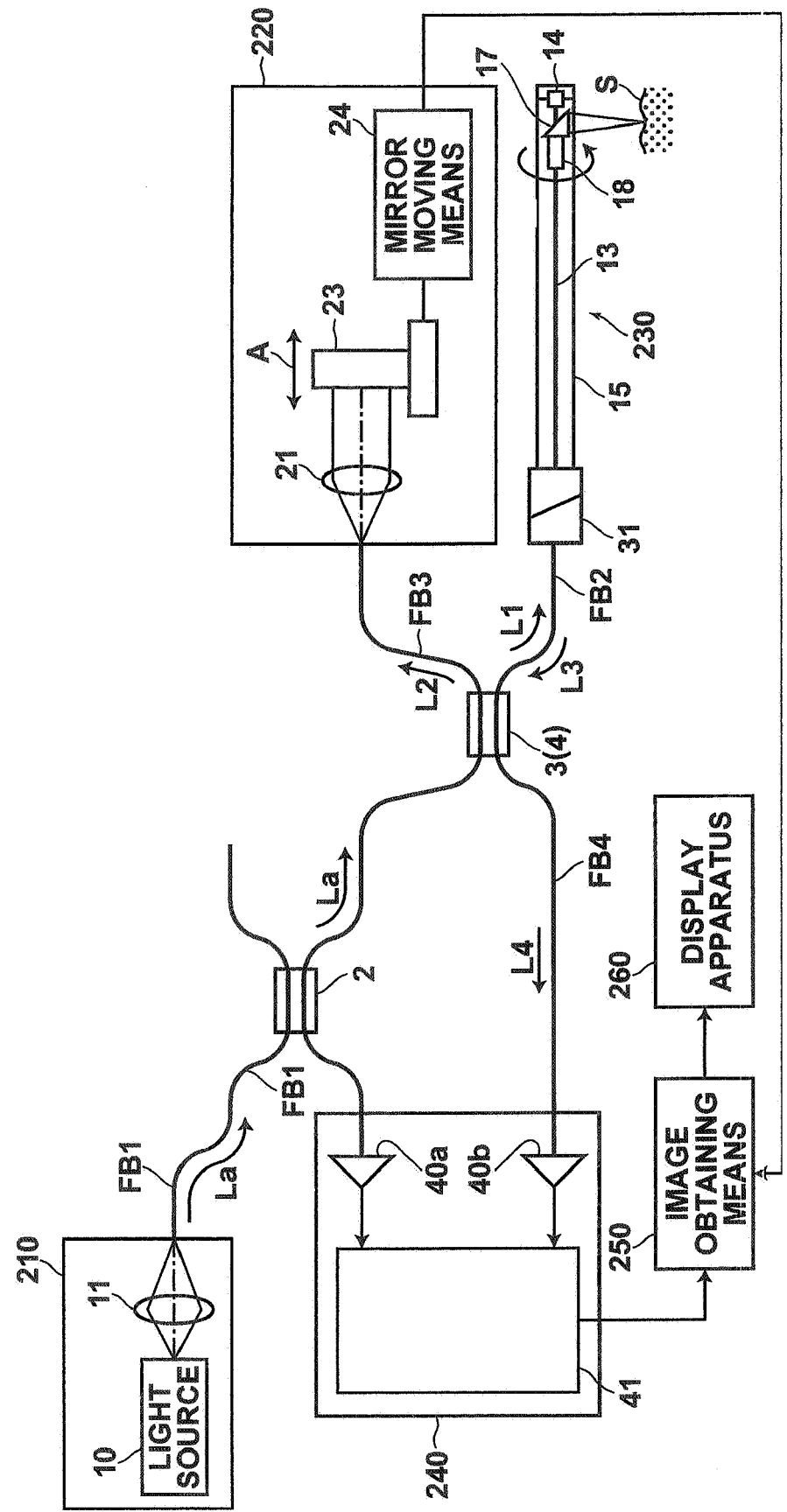
FIG. 9 is a schematic diagram that illustrates the construction of an optical tomography apparatus according to an embodiment of the present invention.

Hereinafter, an optical tomography apparatus 200 according to a first embodiment of the present invention will be described with reference to FIG. 9. FIG. 9 is a schematic diagram that illustrates the construction of the optical tomography apparatus 200.

The optical tomography apparatus 200 illustrated in FIG. 9 obtains tomographic images of measurement targets by the aforementioned TD-OCT measurement technique. The optical tomography apparatus 200 comprises: a light source unit 210, constituted by a light source 10 that emits a laser light beam La and a condensing lens 11; an optical fiber FB1; a light dividing means 2, for dividing the laser light beam La, which is emitted from the light source unit 210 and propagates through the optical fiber FB1; a light dividing means 3, for dividing the laser beam La, which has passed through the light dividing means 2, into a measuring light beam L1 and a reference light beam L2; an optical fiber FB3; an optical path length adjusting means 220, for adjusting the optical path length of the reference light beam L2, which propagates through the optical fiber FB3; an optical fiber FB2; an optical probe 230 that irradiates the measuring light beam L1, which propagates through the optical fiber FB2, onto a measurement target Sb; a multiplexing means 4 (the light dividing means 3 functions as the multiplexing means 4), for multiplexing a reflected light beam L3, which is the measuring light beam L1 reflected from the measurement target Sb, and the reference light beam L2; and a coherent light detecting means 240, for detecting a coherent light beam L4, formed by multiplexing the reflected light beam L3 and the reference light beam L2.

The light source unit 210 comprises: an SLD (Super Luminescent Diode) that emits a low coherence light beam La having a central wavelength λc of 1.1 μm and a full width at half maximum spectrum Δλ of 90 nm as the light source 10; and the condensing lens 11, for causing the light beam La emitted from the light source 10 to enter the optical fiber FB1 as an optical system. Note that the detailed construction of the SLD will be described later.

The optical path length adjusting means 220 comprises: a collimating lens 21, for collimating the reference light beam L2 emitted from the optical fiber FB3; a mirror 23, which is movable in the directions indicated by arrow A, for varying the distance between it and the collimating lens 21; and a mirror moving means 24, for moving the mirror 23. The optical path length adjusting means 220 functions to change the optical path length of the reference light beam L2, to vary the measurement position within the measurement target Sb in the depth direction. The reference light beam L2, of which the optical path length has been varied, is guided to the multiplexing means 4.

The optical probe 230 comprises: a probe outer cylinder 15, which has a closed distal end; a single optical fiber 13, which is provided to extend along the axial direction of the outer cylinder 15 within the interior space thereof; a prism mirror 17, for deflecting a light beam L emitted from the distal end of the optical fiber 15; a rod lens 18, for condensing the light beam L such that it converges on the measurement target Sb, which surrounds the outer cylinder 15; and a motor 14, for rotating the prism mirror 17 with the axis of the optical fiber 13 as the rotational axis.

The light dividing means 3 is constituted by a 2×2 optical fiber coupler, for example. The light dividing means 3 functions to divide the light beam La emitted by the light source unit 210 and guided through the optical fiber FB1 into the measuring light beam L1 and the reference light beam L2. The light dividing means 3 is optically connected to the optical fibers FB2 and FB3. The measuring light beam L1 is guided through the optical fiber FB2, and the reference light beam L2 is guided through the optical fiber FB3. Note that the light dividing means 3 of the present embodiment also functions as the multiplexing means 4.

The optical fiber FB2 is optically connected to the optical probe 230, and the measuring light beam is guided through the optical fiber FB2 to the optical probe 230. The optical probe 230 is to be inserted into body cavities via a forceps opening and a forceps channel, and is removably mounted to the optical fiber FB2 with an optical connector 31.

The multiplexing means 4 is constituted by the aforementioned 2×2 optical coupler. The multiplexing means 4 multiplexes the reference light beam L2, of which the frequency has been shifted and the optical path length has been adjusted by the optical path length adjusting means 220, and the reflected light beam L3 reflected by the measurement target Sb. The multiplexed coherent light beam L4 is emitted toward the coherent light detecting means 240 via the optical fiber FB4.

The coherent light detecting means 240 detects the intensity of the coherent light beam L4. The coherent light detecting means 240 comprises: photodetectors 40a and 40b, for measuring the intensity of the coherent light beam L4; and a calculating section 41, for adjusting the input balance of detection values obtained by the photodetectors 40a and 40b, to enable balanced detection. Specifically, an interference signal of an amplitude proportionate to the amount of reflected light is detected only in cases in which the difference between the total of the entire optical path length of the measuring light beam L1 and that of the reflected light beam L3, which is reflected or backward scattered at a point within the measurement target Sb, and the optical path length of the reference light beam L2 is shorter than the coherence length of the light source. By varying the optical path length with the optical path length adjusting means 220, the position of the reflective point (depth) within the measurement target Sb from which interference signals can be obtained is varied. Thereby, the coherent light detecting means 240 is configured to obtain reflective rate signals from each measuring position within the measurement target Sb. Note that information regarding the measurement position is output to an image obtaining means 250 from the optical path length adjusting means 220. The image obtaining means 250 obtains reflected light intensity distribution data, based on the information regarding the measurement position output by the mirror moving means 24 and the signal detected by the coherent light detecting means 240.

Hereinafter, the operation of the optical tomography apparatus 200 of the above construction will be described. When obtaining a tomographic image, first, the mirror 23 is moved in the direction of arrow A, to adjust the optical path length such that the measurement target Sb is positioned within a measurable region. Thereafter, the light beam La is emitted from the light source unit 210. The light beam La is divided into the measuring light beam L1 and the reference light beam L2 by the light dividing means 3. The measuring light beam L1 is emitted within the body cavity from the optical probe 230, and irradiated on the measurement target Sb.

The reflected light beam L3, reflected by the measurement target Sb, is multiplexed with the reference light beam L2, reflected by the mirror 23, to form the coherent light beam L4.

The coherent light beam L4 is divided into two light beams by the light dividing means 3 (the multiplexing means 4). A first light beam is input to the photodetector 40a, and a second light beam is input to the photodetector 40b.

The coherent light detecting means 240 performs balanced detection, by adjusting the input balance of detection values obtained by the photodetectors 40a and 40b. The intensity of the coherent light beam L4 is detected, and output to the image obtaining means 250.

The image obtaining means obtains reflected light intensity data regarding a predetermined depth within the measurement target Sb, based on the detected intensity of the coherent light beam L4. Next, the optical path length adjusting means 220 changes the optical path length of the reference light beam L2, and the intensity of the coherent light beam L4 is detected, to obtain reflected light intensity data regarding a different depth within the measurement target Sb. By repeating the above operations, reflected light intensity data in the depth direction (one-dimensional) of the measurement target Sb is obtained.

Next, the motor 14 of the optical probe 230 rotates the prism mirror 17, thereby scanning the measuring light beam L1 on the measurement target Sb. Thereby, data in the depth direction along the scanning direction can be obtained, and a tomographic image of tomographic sections that include the scanning direction can be obtained. The tomographic image obtained in this manner is displayed at a display apparatus 260. Note that by moving the optical probe 230 in the horizontal direction in FIG. 9, the measuring light beam L1 can be scanned in a second direction perpendicular to the aforementioned scanning direction. Thereby, a tomographic image of tomographic sections that include the second direction can be further obtained.

In the case that a light beam having a central wavelength λc of 1.1 μm and a full width at half maximum spectrum Δλ of 90 nm is employed as the low coherence light beam La, the measuring light beam L1, the reference light beam L2, and the reflected light beam L3 will have a central wavelength λc of 1.1 μm, and a full width at half maximum spectrum Δλ of 90 nm. Therefore, λc²/Δλ becomes 13.9. Accordingly, if the effects of dispersion are taken into consideration, a central wavelength band of 1.0 μm is superior to a central wavelength band of 1.3 μm. In addition, in this case, the central wavelength λc and the full width at half maximum spectrum Δλ satisfies the conditions:

λc+(Δλ/2)≦1.2 μm

λc−(Δλ/2)≧0.98 μm.

Therefore, the measuring light beam L1 has good transmissivity with respect to the measurement target Sb, and the influence exerted on the reflected light beam L3 by the light absorption peaks of water at the wavelengths of 0.98 μm and 1.2 μm is decreased. Accordingly, high resolution optical tomographic images having high image quality can be obtained.

Figure 10:
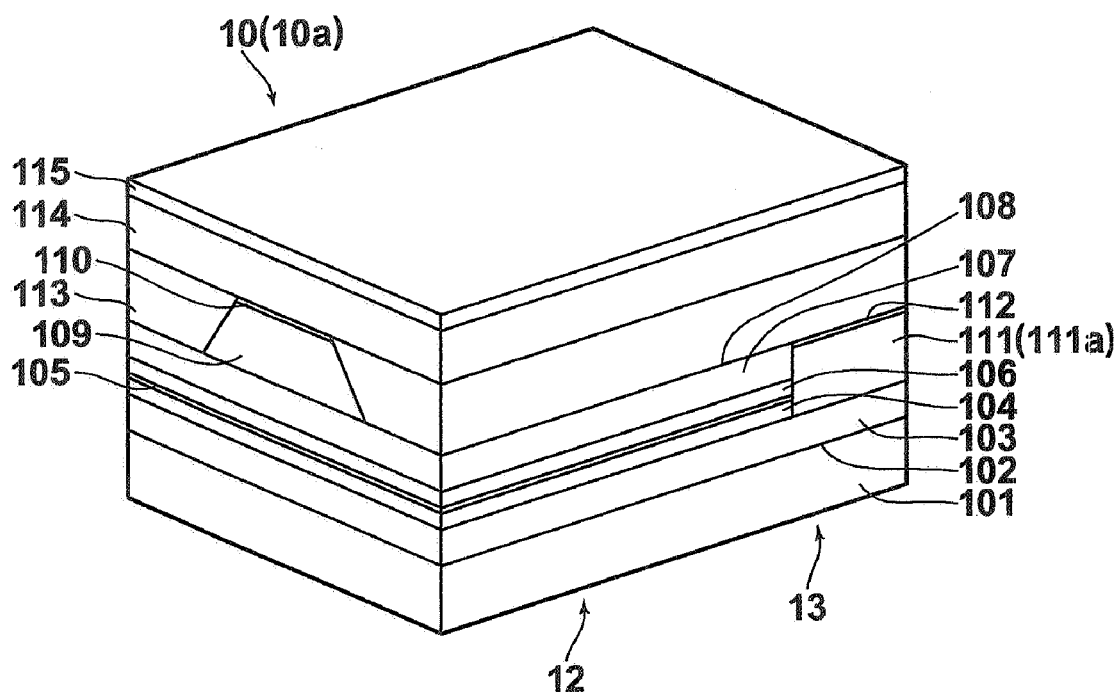
FIG. 10 is a schematic diagram that illustrates the construction of an SLD.

Next, the SLD 10 of the light source unit 210 will be described with reference to FIG. 10. The SLD 10 is a super luminescent diode having an SBR structure formed by crystal growth using the metal organic chemical vapor deposition method (MOCVD). FIG. 10 is a sectional view of the SLD 10. TEG (tri ethyl gallium), TMA (tri methyl aluminum), TMI (tri methyl indium), AsH₃ (arsine), PH₃ (phosphine), and the like are used as the source gas in the MOCVD method. SiH₄ (silane) and DEZ (di ethyl zinc) are employed as dopants.

The SLD 10 comprises: an optical waveguide path section 12; and a window section 13, which is provided at an end opposite a light emitting end of the optical waveguide path section 12. The optical waveguide path section 12 has an SBR structure comprising: a p-type GaAs etching stop layer 108; and a ridge-shaped p-type $In_{0.49}Ga_{0.51}P$ second upper cladding layer 109 formed on the etching stop layer 108. The second upper cladding layer 109 functions as an optical guide.

The SLD is formed by an n-type GaAs substrate 101, on which an n-type GaAs buffer layer 102 and an n-type $In_{0.49}Ga_{0.51}P$ cladding layer 103 are stacked in this order. The optical waveguide path section 12 is formed by: a non-doped GaAs lower optical guiding layer 104; an InGaAs multiple quantum well active layer 105; a non-doped GaAs upper optical guiding layer 106; a p-type $In_{0.49}Ga_{0.51}P$ first upper cladding layer 107, and the GaAs etching stop layer 108, which are stacked on the lower cladding layer 103 in this order. Note that an $In_xGa_{1-x}As$ composition having a ratio In:X>0.3 is employed as the material of the InGaAs multiple quantum well active layer 105.

The ridge-shaped p-type $In_{0.49}Ga_{0.51}P$ second upper cladding layer 109 is formed on the p-type GaAs etching stop layer 108. An n-$In_{0.49}(Al_{0.12}Ga_{0.88})_{0.51}P$ current blocking layer 113 is formed on the sides of the ridge (the p-type $In_{0.49}Ga_{0.51}P$ second upper cladding layer 109). A p-type GaAs cap layer 110 (0.1 μm thick, with a carrier density of $7.0 \times 10^{17}$ cm$^{-3}$); a p-type $In_{0.49}(Al_{0.12}Ga_{0.88})_{0.51}P$ third upper cladding layer 114; and a p-GaAs contact layer 115 are formed on the upper surfaces of the ridge and the n-$In_{0.49}(Al_{0.12}Ga_{0.88})_{0.51}P$ current blocking layer 113.

The window section 13 is formed by a p-type GaAs window region layer 111; an $In_{0.49}Ga_{0.51}P$ window region layer etching stop layer 112; the n-$In_{0.49}(Al_{0.12}Ga_{0.88})_{0.51}P$ current blocking layer 113; the p-type $In_{0.49}(Al_{0.12}Ga_{0.88})_{0.51}P$ third upper cladding layer 114; and the p-GaAs contact layer 115, which are stacked in this order on the n-type $In_{0.49}Ga_{0.51}P$ lower cladding layer.

In the SLD 10 having the construction described above, light, which is guided through the InGaAs multiple quantum well active layer 105 toward the window section 13, is emitted within the window region layer 111 and scattered. Thereby, laser oscillation is suppressed, and a super luminescent light beam having a wide full width at half maximum spectrum is emitted from the light emitting end. The SLD 10 emits a 30 mW super luminescent light beam having a central wavelength of 1.1 μm and a full width at half maximum spectrum of 90 nm.

The window region 111 of the SLD 10 is formed by p-type GaAs having a greater energy gap and a smaller refractive index than the InGaAs multiple quantum well active layer 105, with a lattice coefficient that lattice matches with GaAs within a range of ±0.1% and does not contain Al. Thereby, favorable crystal film qualities are realized in the window region layer 111 and the InGaAs multiple quantum well active layer 105. This extends the life of the element that emits a high output super luminescent light beam that has an undistorted sectional beam shape.

The SLD 10 is not exposed to an environment over 650° after formation of the InGaAs multiple quantum well active layer 105. Therefore, the InGaAs multiple quantum well active layer 105 does not deteriorate, and high output can be maintained for long periods of time.

Note that an SLD 10a having a p-type $In_{0.49}Ga_{0.51}P$ window region layer 111a may be employed instead of the SLD 10. P-type $In_{0.49}Ga_{0.51}P$ is also a semiconductor material which has a greater energy gap and a lower refractive index than the InGaAs multiple quantum well active layer 105 that lattice matches with GaAs within a range of ±0.1% and does not contain Al. The SLD 10a can also emit a high output super luminescent light beam having a central wavelength of 1.1 μm and a full width at half maximum spectrum of 90 nm, which has an undistorted sectional beam shape. In addition, the SLD 10a was continuously driven at room temperature to evaluate the element life thereof. Output levels fell to 90% of the initial output after approximately 5000 hours.

Figure 11:
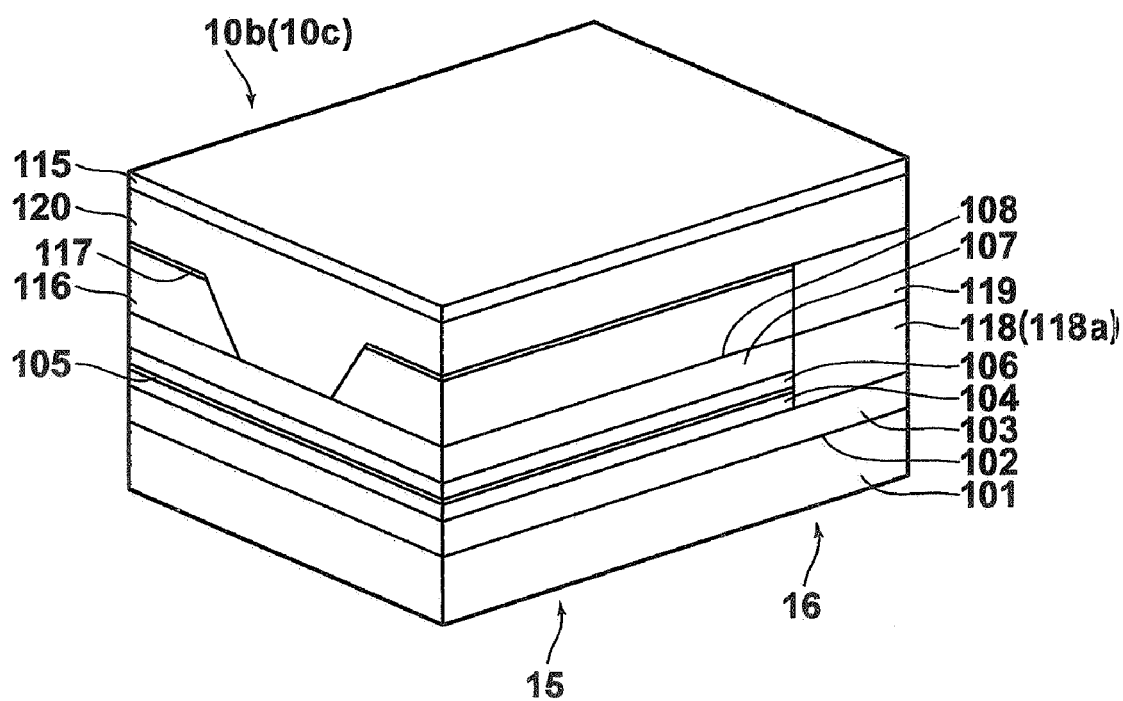
FIG. 11 is a schematic diagram that illustrates the construction of an alternate SLD.

As a further alternative, an SLD 10b having an inner stripe structure as illustrated in FIG. 11 may be employed instead of the SLD 10. As illustrated in FIG. 11, the SLD 10b comprises: an optical waveguide path section 15; and a window section 16, which is provided at an end opposite a light emitting end of the optical waveguide path section 15. The optical waveguide path section 15 is of an inner stripe structure, wherein 3 mm wide stripe structures formed on a p-type GaAs etching stop layer 108 constrict the flow of current. In addition, an n-type $(Al_{0.33}Ga_{0.67})_{0.5}As$ current blocking layer 119 (0.5 μm thick, with a carrier density of $7.0 \times 10^{17}$ cm$^{-3}$) is formed above a p-type GaAs window region layer 118 (0.5 μm). The other structures are substantially the same as those of the SLD 10. An SLD 10c that comprises a p-type $In_{0.49}Ga_{0.51}P$ window region layer 118a may also be employed.

By employing the light source unit 210 comprising such SLD's, the reliability of the light source unit 210 is improved, and as a result, the reliability of the optical tomography apparatus 200 is also improved.

Note that the SLD 10 and the SLD 10b have SBR structures, while the SLD 10b and the SLD 10c have inner stripe structures. However, the structure of the SLD is not limited to these two examples. The SLD may have other index guide structures or gain guide structures.

Figure 12:
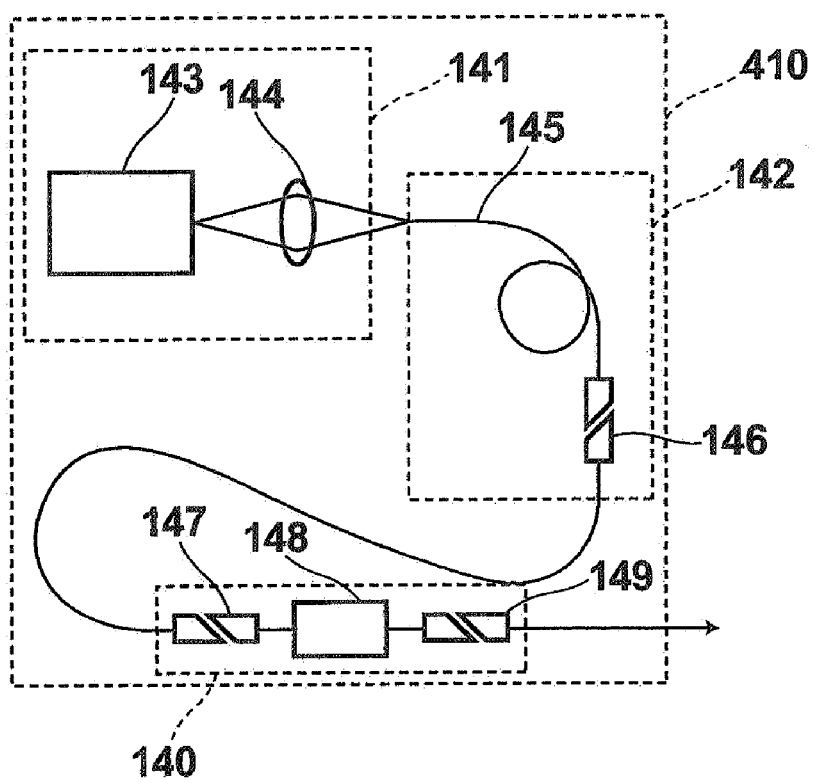
FIG. 12 is a schematic diagram that illustrates the construction of a first alternate light source unit.

Note that a light source unit 410, such as that illustrated in FIG. 12, may be considered for use instead of the light source unit 210. The light source unit 410 comprises: a pulse light source 141 that employs a mode locked solid state laser 143;

a pulse compressing section 142; and a spectrum forming section 140. The pulse light source 141 comprises: the mode locked solid state laser 143; and a condensing lens 144, for guiding the pulse light beams emitted from the mode locked solid state laser 143 to the pulse Compressing section 142. The pulse compressing section 142 comprises: a photonic crystal fiber 145 having negative dispersion properties; and an optical connector 146. The structural dispersion values of photonic crystal fibers are selectable. Therefore, negative dispersion properties can be realized with respect to a desired wavelength band. The spectrum forming section 140 comprises: an optical connector 147; a Gaussian distribution forming filter 148, for causing the spectrum shape of the wide band light beam output from the pulse compressing section 142 to become a Gaussian distribution; and an optical connector 149 for guiding the low coherence light beam, which has passed through the Gaussian distribution forming filter 148, to the fiber FB1. Note that the Gaussian distribution forming filter 148 forms the spectrum shape of the low coherence light beam such that the following conditions are satisfied.

$$\lambda c^2/\Delta\lambda \leq 15$$

$$\lambda c + (\Delta\lambda/2) \leq 1.2 \ \mu m$$

$$\lambda c - (\Delta\lambda/2) \geq 0.98 \ \mu m$$

Figure 13:
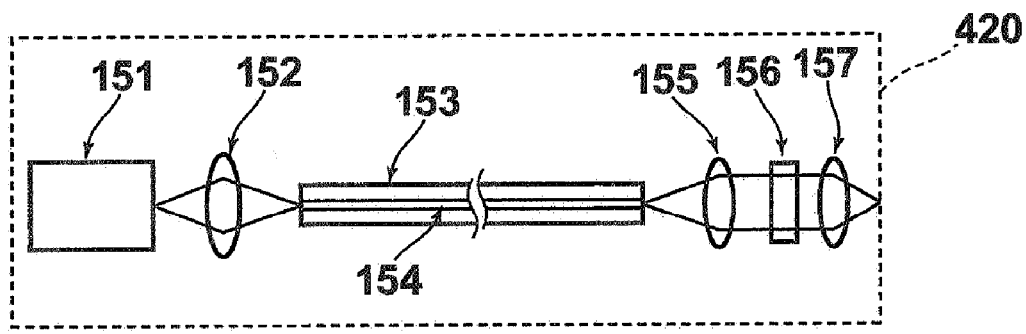
FIG. 13 is a schematic diagram that illustrates the construction of a second alternate light source unit.

As still another alternative, a light source unit 420 that comprises phosphor that contains near infrared fluorescent pigment, such as that illustrated in FIG. 13, may be employed instead of the light source unit 210.

Figure 14:
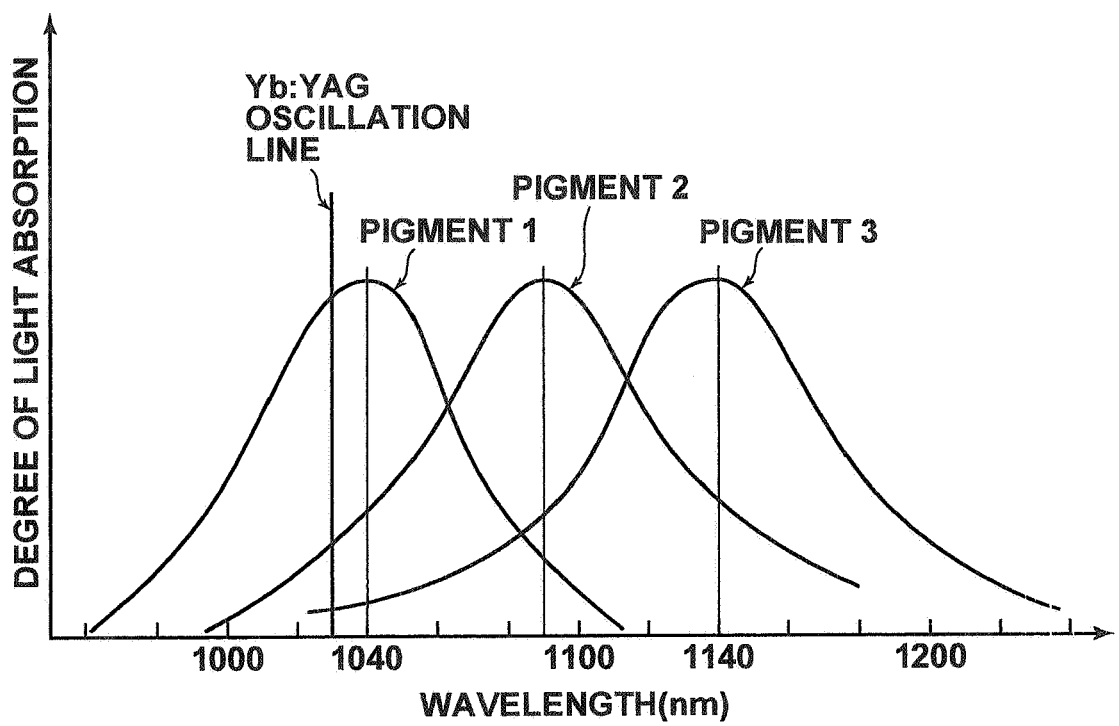
FIG. 14 is a graph for explaining absorption spectra of pigments.
Figure 15:
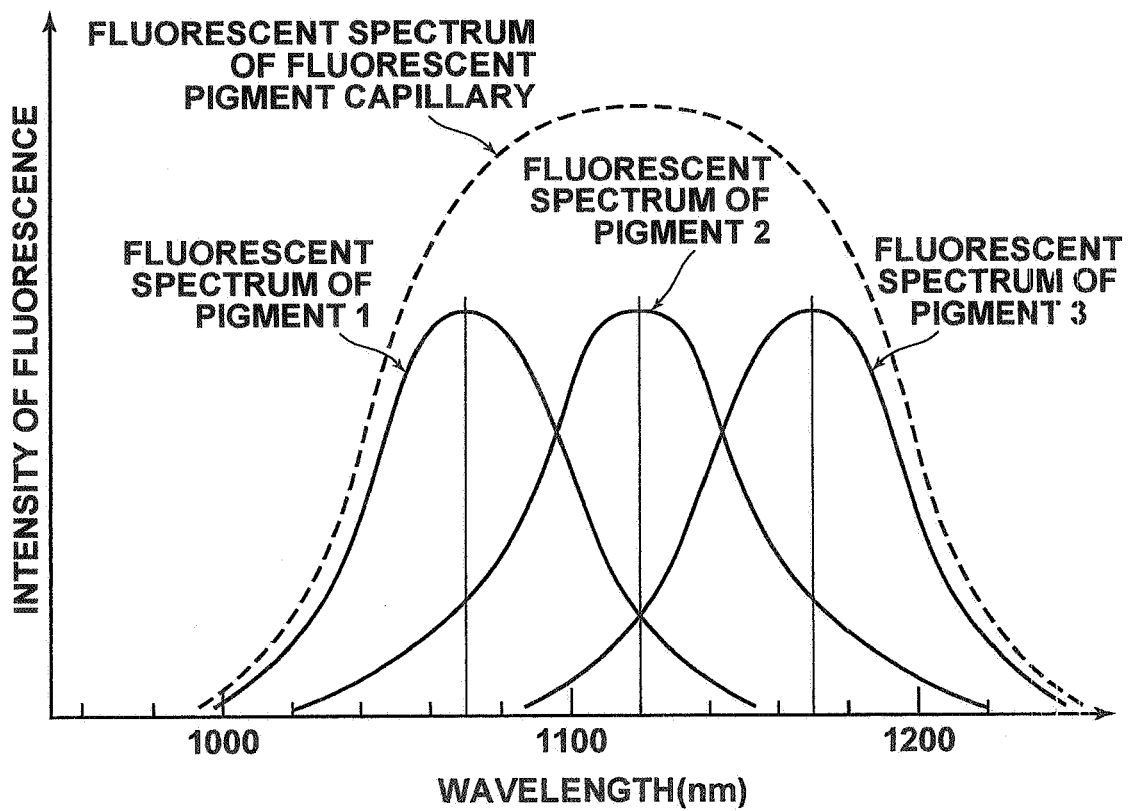
FIG. 15 is a graph for explaining fluorescence.

The light source unit 420 comprises: a capillary 153 that functions as the phosphor; a Yb:YAG laser 151 for exciting the capillary 153; an excitation light cutoff filter 156; and lenses 152, 155, and 157. Pigment, which is excitable by light having wavelengths within a range of 1.0 to 1.2 μm, is sealed within the capillary 153 along with a solvent. Absorption spectra of pigments 1, 2, and 3 are illustrated in the graph of FIG. 14. The pigments 1, 2, and 3 are excited by a light beam having a wavelength of 1.03 μm emitted by the Yb:YAG laser. The fluorescence illustrated in FIG. 15 can be obtained, by adjusting the concentration of each pigment such that the intensities of fluorescence are substantially equal among the three pigments. The sum of the fluorescence from each of the three pigments is a 1000 nm to 1200 nm spectrum as represented by the broken line in FIG. 15. The wide band light beam generated in this manner passes through the lens 155, the excitation light cutoff filter 156 and the lens 157, and is guided to the fiber FB1 as the low coherence light beam La. Note that the excitation light cutoff filter 156 is provided to prevent the excitation light emitted from the Yb:YAG laser from entering the fiber FB1.

Figure 16:
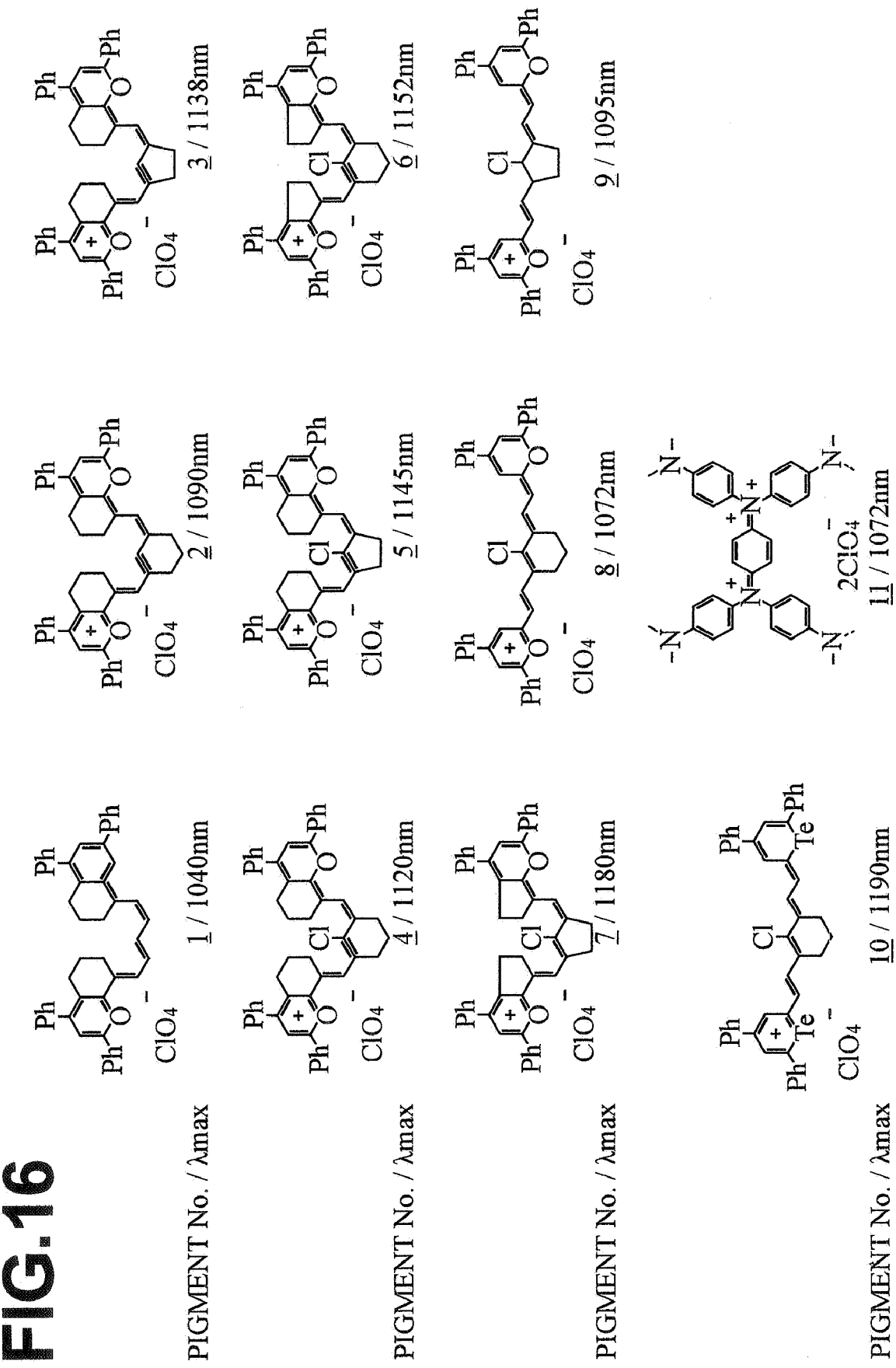
FIG. 16 illustrates examples of pyrylium type pigment.

Pyrylium pigments, such as those illustrated in FIG. 16, may be employed as the fluorescent pigment. Other appropriate lasers for emitting excitation light, such as an Nd:YLF laser that emits laser beams having a wavelength of 1.04 μm and an Nd:YAG laser that emits laser beams having a wavelength of 1.064 μm, can be selected depending on the combination of pigments.

Figure 17:
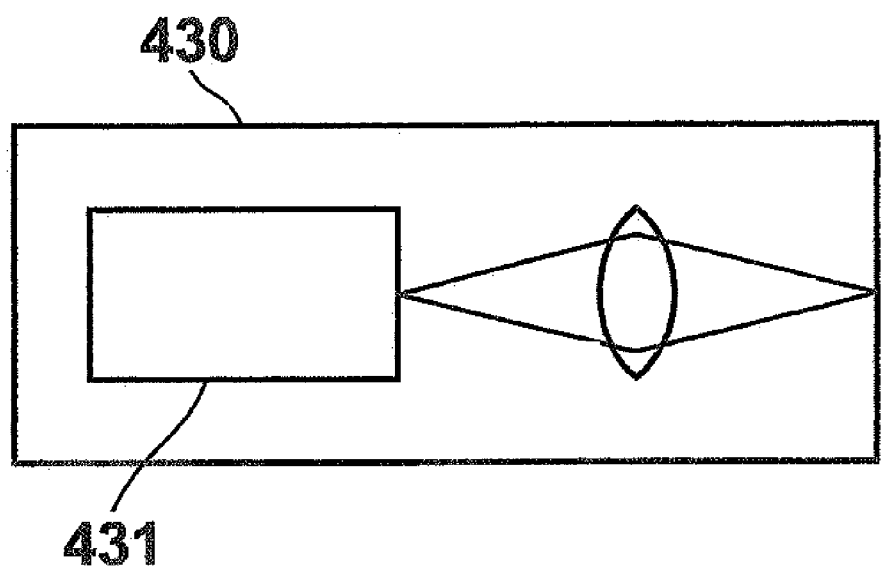
FIG. 17 is a schematic diagram that illustrates the construction of a third alternate light source unit.

As a still further modification of the present embodiment, a light source unit 430, such as that illustrated in FIG. 17, may be employed instead of the light source unit 210. The light source unit 430 comprises: a Yb type pulse laser, an Nd type pulse laser, or a Ti type pulse laser as a light source 431. A Yb:YAG laser, a Yb:glass laser, or a Yb type fiber laser may be utilized as the Yb type pulse laser. An Nd:YAG laser, an Nd:glass laser, or an Nd:fiber laser may be utilized as the Nd type pulse laser.

Figure 18:
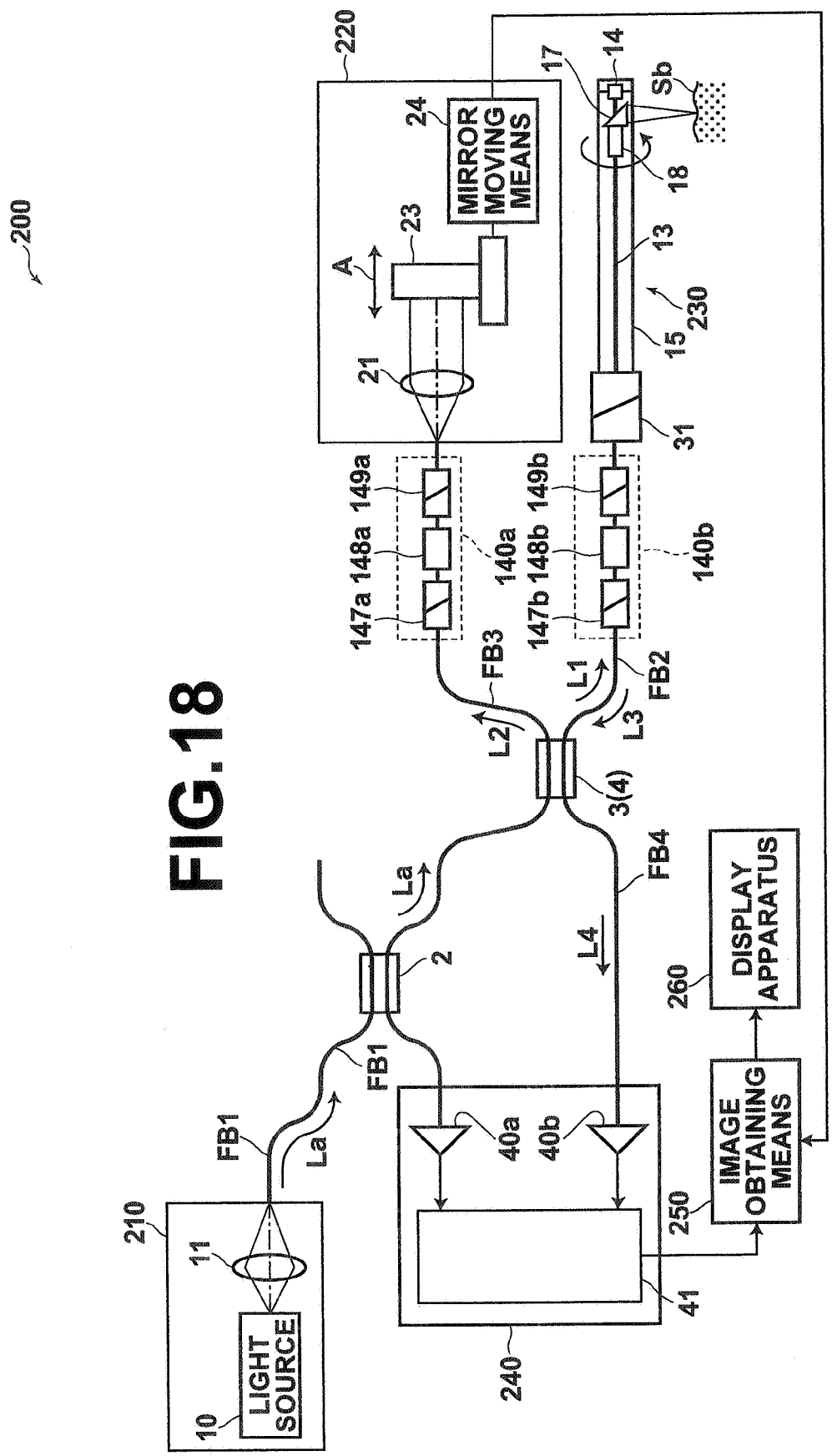
FIG. 18 is a schematic diagram that illustrates a modified optical tomography apparatus.

Note that the spectrum forming section 140 comprising the Gaussian distribution forming filter 148 may be provided in all of the aforementioned light source units 210, 420, and 430, in a manner similar to the light source unit 410. The spectrum forming section 140 may be provided at any position in the optical paths of the reference light beam L2 and the reflected light beam L3 prior to multiplexing. For example, a spectrum forming section 140a comprising: an optical connector 147a; a Gaussian distribution forming filter 148a; and an optical connector 149a may be provided along the optical path of the reference light beam L2, and a spectrum forming section 140b comprising: an optical connector 147b; a Gaussian distribution forming filter 148b; and an optical connector 149b may be provided along the optical path of the measuring light beam L1 (the reflected light beam L3), as illustrated in FIG. 18.

In the case that the Gaussian distribution forming filter 148 is provided, the following conditions should be satisfied.

$$\lambda c^2/\Delta\lambda \leq 15$$

$$\lambda c + (\Delta\lambda/2) \leq 1.2 \ \mu m$$

$$\lambda c - (\Delta\lambda/2) \geq 0.98 \ \mu m$$

That is, as long as the low coherence light beam satisfies the above conditions after passing through the Gaussian distribution forming filter 148, the light beam emitted from the SLD, the mode locked solid state laser, the phosphor that contains near infrared fluorescent pigment, or the pulse laser may have any central wavelength λc and any full width at half maximum spectrum Δλ. Note that in the case that the two Gaussian distribution forming filters 148a and 148b are provided, it is preferable that the filter properties are substantially uniform. However, the filter properties may be different, as long as no adverse effects are exerted on measurement of the intensity of the coherent light beam.

Figure 19:
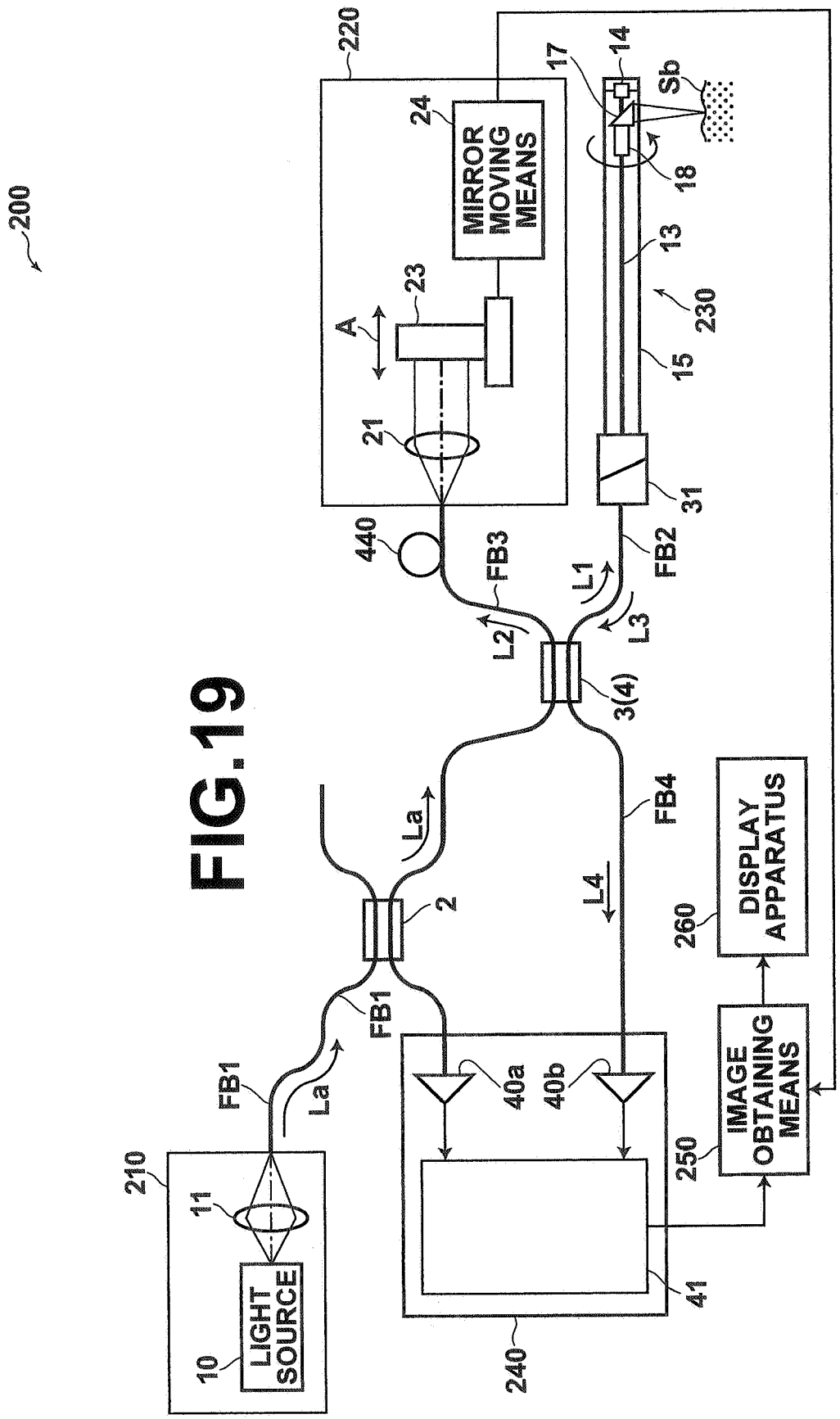
FIG. 19 is a schematic diagram that illustrates another modified optical tomography apparatus.

Further, a phase modulator 440, for slightly shifting the frequency of the reference light beam L2 may be provided along the optical path thereof (the optical fiber FB3), as illustrated in FIG. 19. In this case, the coherent light detecting means 240 can detect the intensity of the coherent light beam L4, which has propagated through the optical fiber FB2 from the multiplexing means 4, by heterodyne detection, for example. Specifically, if the sum of the optical path lengths of the measuring light beam L1 and the reflected light beam L3 is equal to the optical path length of the reference light beam L2, a beat signal that varies in intensity is generated due to the frequency difference between the reference light beam L2 and the reflected light beam L3. By detecting this beat signal, the intensity of the coherent light beam L4 can be detected with high accuracy.

Figure 20:
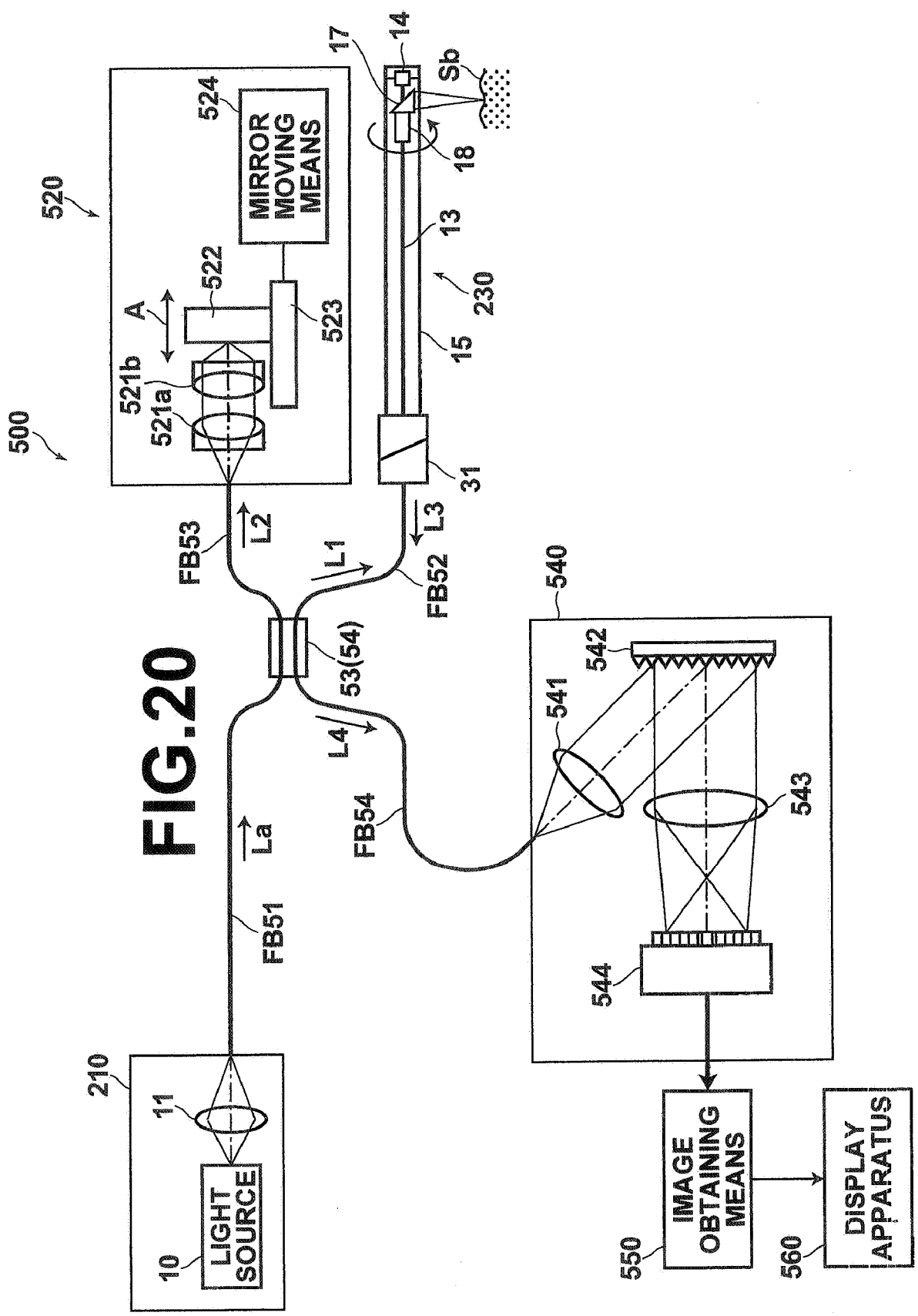
FIG. 20 is a schematic diagram that illustrates an optical tomography apparatus according to a second embodiment of the present invention.

Next, an optical tomography apparatus 500 according to a second embodiment of the of the present invention will be described with reference to FIG. 20. FIG. 20 is a schematic diagram that illustrates the optical tomography apparatus 500 according to the second embodiment of the present invention. Note that structural elements which are the same as those illustrated in FIG. 9 are denoted by the same reference numerals, and detailed descriptions thereof will be omitted, insofar as they are not particularly necessary. The optical tomography apparatus 500 illustrated in FIG. 20 obtains tomographic images of measurement targets, such as the interiors of body cavities of living organisms or cells, by the aforementioned SD-OCT measurement technique. The optical tomography apparatus 500 comprises: a light source unit 210, for emitting a low coherence light beam La; a light dividing means 53, for dividing the low coherence light beam La, which is emitted from the light source unit 210, into a measuring light beam L1 and a reference light beam L2; an optical path length adjusting means 520, for adjusting the optical path length of the reference light beam L2; an optical probe 230 that irradiates the measuring light beam L1 onto a measurement target Sb; a multiplexing means 54, for multiplexing a reflected light beam L3, which is the measuring light beam L1 reflected from the measurement target Sb, and the reference light beam L2; and a coherent light detecting means 540, for detecting a coherent light beam L4, formed by multiplexing the reflected light beam L3 and the reference light beam L2.

The light dividing means 53 is constituted by a 2×2 optical fiber coupler, for example. The light dividing means 53 functions to divide the light beam La emitted by the light source unit 210 and guided through an optical fiber FBS1 into the measuring light beam L1 and the reference light beam L2. The light dividing means 53 is optically connected to optical fibers FB52 and FB53. The measuring light beam L1 is guided through the optical fiber FB52, and the reference light beam L2 is guided through the optical fiber FB53. Note that the light dividing means 53 of the present embodiment also functions as the multiplexing means 54.

The optical fiber FB52 is optically connected to the optical probe 230, and the measuring light beam is guided through the optical fiber FB52 to the optical probe 230.

The optical path length adjusting means 520 is provided at the reference light beam L2 emitting side of the optical fiber FB53. The optical path length adjusting means 520 adjusts the optical path length of the reference light beam L2 to adjust the position at which obtainment of tomographic images is initiated. The optical path length adjusting means 520 comprises: a mirror 522, for reflecting the reference light beam L2 emitted from the optical fiber FB53; a first optical lens 521a, which is provided between the mirror 522 and the optical fiber FB53; and a second optical lens 521b, which is provided between the first optical lens 521a and the mirror 522.

The first optical lens 521a functions to collimates the reference light beam L2, which is emitted from the core of the optical fiber FB53, and also functions to focus the reference light beam L2, which is reflected by the mirror 522, onto the core of the optical fiber FB53. The second optical lens 521b functions to focus the reference light beam L2, which is collimated by the first optical lens 521a, onto the mirror 522, and also functions to collimate the reference light beam L2, which is reflected by the mirror 522. That is, the first optical lens 521a and the second optical lens 521b form a confocal optical system.

Accordingly, the reference light beam L2 emitted from the optical fiber FB53 is collimated by the first optical lens 521a, and focused onto the mirror 522 by the second optical lens 521b. Thereafter, the reference light beam L2 reflected by the mirror 522 is collimated by the second optical lens 521b, and focused onto the core of the optical fiber FB53 by the first optical lens 521a.

The optical path length adjusting means 520 further comprises: a base 23, on which the second optical lens 521b and the mirror 522 are fixed; and a mirror moving means 24, for moving the base 23 in the direction of the optical axis of the first optical lens 521a. The optical path length of the reference light beam L2 is varied by moving the base 23 in the directions indicated by arrow A.

The multiplexing means 54 is constituted by the aforementioned 2×2 optical coupler. The multiplexing means 54 multiplexes the reference light beam L2, of which the optical path length has been adjusted by the optical path length adjusting means 520, and the reflected light beam L3 reflected by the measurement target Sb. The multiplexed coherent light beam L4 is emitted toward the coherent light detecting means 540 via the optical fiber FB4.

The coherent light detecting means 540 detects the intensity of the coherent light beam L4. The coherent light detecting means 540 comprises: a collimating lens 541, for collimating the coherent light beam L4 emitted from the optical fiber FB4; a spectral decomposing means 542, for decomposing the coherent light beam L4 into each of its constituent wavelength bands; and a photodetecting means 544, for detecting each wavelength band of the coherent light beam L4.

The spectral decomposing means 542 is constituted by a diffraction grating element or the like. The spectral decomposing means 542 decomposes the coherent light beam L4 incident thereon, and emits the decomposed components toward the photodetecting means 544. The photodetecting means 544 is constituted by CCD elements or the like, in which optical sensors are arranged one dimensionally or two dimensionally. Each of the optical sensors are configured to detect each wavelength band component of the spectrally decomposed coherent light beam L4, respectively.

The photodetecting means 544 is connected to an image obtaining means 550, constituted by a computer system such as a personal computer. The image obtaining means 550 is connected to a display apparatus 560, constituted by a CRT display or an LCD.

Hereinafter, the operation of the optical tomography apparatus 500 of the above construction will be described. When obtaining a tomographic image, first, the base 23 is moved in the direction of arrow A, to adjust the optical path length such that the measurement target Sb is positioned within a measurable region. Thereafter, the light beam La is emitted from the light source unit 210. The light beam La is divided into the measuring light beam L1 and the reference light beam L2 by the light dividing means 53. The measuring light beam L1 is emitted within the body cavity from the optical probe 230, and irradiated on the measurement target Sb. At this time, the measuring light beam L1 is scanned one dimensionally along the measurement target Sb by the aforementioned operation of the optical probe 230. The reflected light beam L3, which is reflected by the measurement target Sb, is multiplexed by the reference light beam L2, which is reflected by the mirror 522, to form the coherent light beam L4. The coherent light beam L4 is detected by the coherent light detecting means 540. The detected coherent light beam L4 undergoes appropriate waveform correction and noise removal at the image obtaining means 550. Then, the coherent light beam L4 undergoes Fourier transform, and reflected light intensity distribution data is obtained regarding the depth direction of the measurement target Sb.

Next, the motor 14 of the optical probe 230 rotates the prism mirror 17, thereby scanning the measuring light beam L1 on the measurement target Sb. Thereby, data in the depth direction along the scanning direction can be obtained, and a tomographic image of tomographic sections that include the scanning direction can be obtained. The tomographic image obtained in this manner is displayed at a display apparatus 560. Note that by moving the optical probe 230 in the horizontal direction in FIG. 20, the measuring light beam L1 can be scanned in a second direction perpendicular to the aforementioned scanning direction. Thereby, a tomographic image of tomographic sections that include the second direction can be further obtained.

In the case that a light beam having a central wavelength $\lambda c$ of 1.1 µm and a full width at half maximum spectrum $\Delta\lambda$ of 90 nm is employed as the low coherence light beam La, $\lambda c^2/\Delta\lambda$ becomes 13.9. Therefore, if the effects of dispersion are taken into consideration, a central wavelength band of 1.0 μm is superior to a central wavelength band of 1.3 μm. In addition, in this case, the central wavelength λc and the full width at half maximum spectrum Δλ satisfies the conditions:

$$\lambda c + (\Delta\lambda/2) \leq 1.2 \ \mu m$$

$$\lambda c - (\Delta\lambda/2) \geq 0.98 \ \mu m.$$

Therefore, the low measuring light beam L1 has good transmissivity with respect to the measurement target Sb, and the influence exerted on the reflected light beam L3 by the light absorption peaks of water at the wavelengths of 0.98 μm and 1.2 μm is decreased. Accordingly, high resolution optical tomographic images having high image quality can be obtained. Note that similarly to the first embodiment, the light source unit 410 illustrated in FIG. 12 may be used instead of the light source unit 210 in the second embodiment as well. The light source unit 410 comprises: the pulse light source 141 that employs a mode locked solid state laser 143; a pulse compressing section 142; and a spectrum forming section 140. The pulse light source 141 comprises: the mode locked solid state laser 143; and a condensing lens 144, for guiding the pulse light beams emitted from the mode locked solid state laser 143 to the pulse compressing section 142. Alternatively, the light source unit 420 that comprises phosphor that contains near infrared fluorescent pigment as illustrated in FIG. 13, may be employed instead of the light source unit 210. As a further alternative, the light source unit 430 illustrated in FIG. 17 may be employed instead of the light source unit 210. The light source unit 430 comprises: a Yb type pulse laser, an Nd type pulse laser, or a Ti type pulse laser as a light source 431. A Yb:YAG laser, a Yb:glass laser, or a Yb type fiber laser may be utilized as the Yb type pulse laser. An Nd:YAG laser, an Nd:glass laser, or an Nd:fiber laser may be utilized as the Nd type pulse laser. Further, the spectrum forming section 140a comprising: the optical connector 147a; the Gaussian distribution forming filter 148a; and the optical connector 149a may be provided along the optical path of the reference light beam L2, and the spectrum forming section 140b comprising: the optical connector 147b; the Gaussian distribution forming filter 148b; and the optical connector 149b may be provided along the optical path of the measuring light beam L1 (the reflected light beam L3), as illustrated in FIG. 18.

Figure 21:
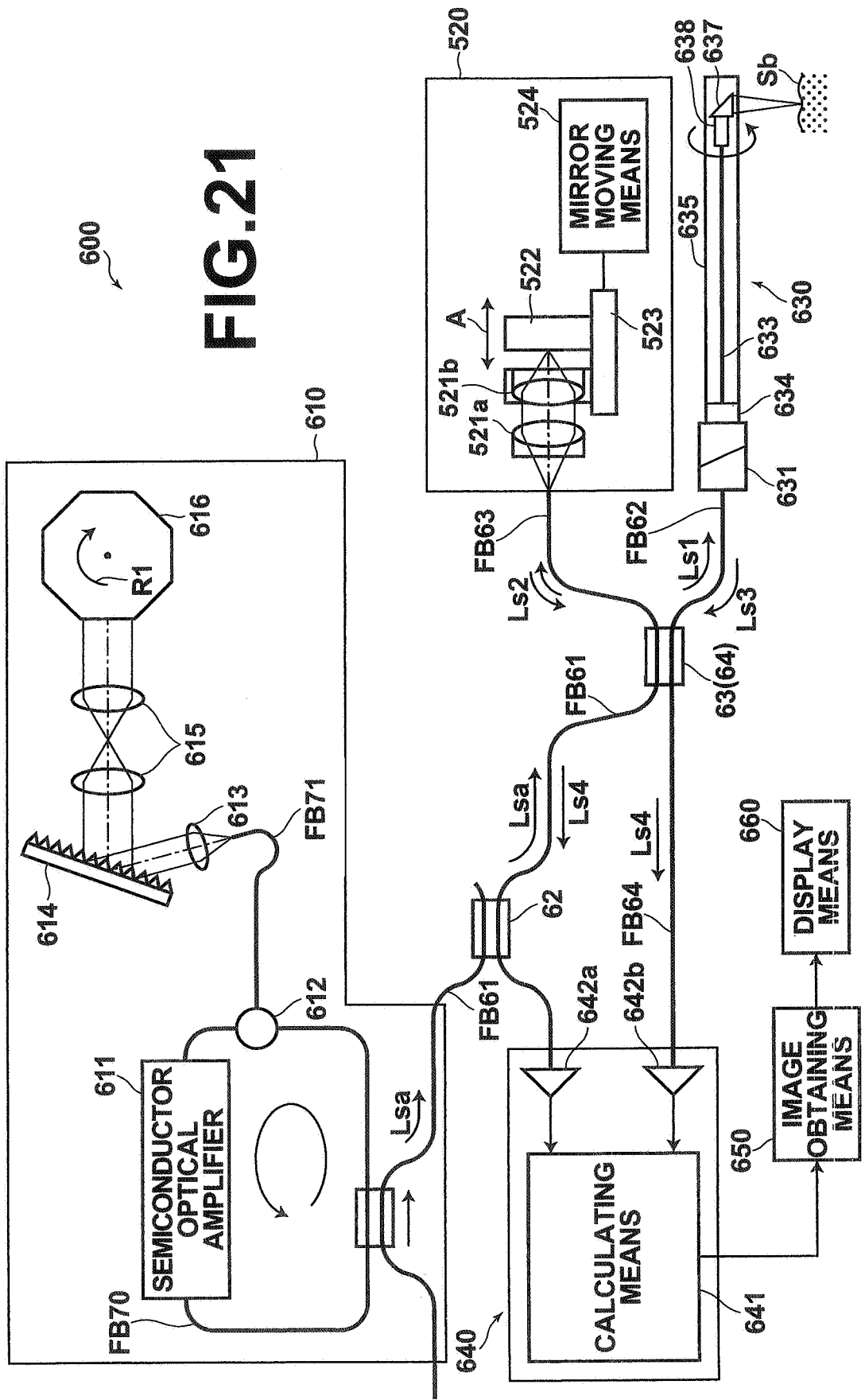
FIG. 21 is a schematic diagram that illustrates an optical tomography apparatus according to a third embodiment of the present invention.

Hereinafter, an optical tomography apparatus 600 according to a third embodiment of the present invention will be described with reference to FIG. 21. FIG. 21 is a schematic diagram that illustrates the construction of the optical tomography apparatus 600.

The optical tomography apparatus 600 illustrated in FIG. 21 obtains tomographic images of measurement targets by the aforementioned SS-OCT measurement technique. The optical tomography apparatus 600 comprises: a light source unit 610, for emitting a laser light beam Ls; a light dividing means 63, for dividing the laser beam Ls into a measuring light beam Ls1 and a reference light beam Ls2; an optical path length adjusting means 520, for adjusting the optical path length of the reference light beam Ls2; an optical probe 630 that irradiates the measuring light beam Ls1 onto a measurement target Sb; a multiplexing means 64, for multiplexing a reflected light beam Ls3, which is the measuring light beam Ls1 reflected from the measurement target Sb, and the reference light beam Ls2; and a coherent light detecting means 640, for detecting a coherent light beam Ls4, formed by multiplexing the reflected light beam Ls3 and the reference light beam Ls2.

Figure 22:
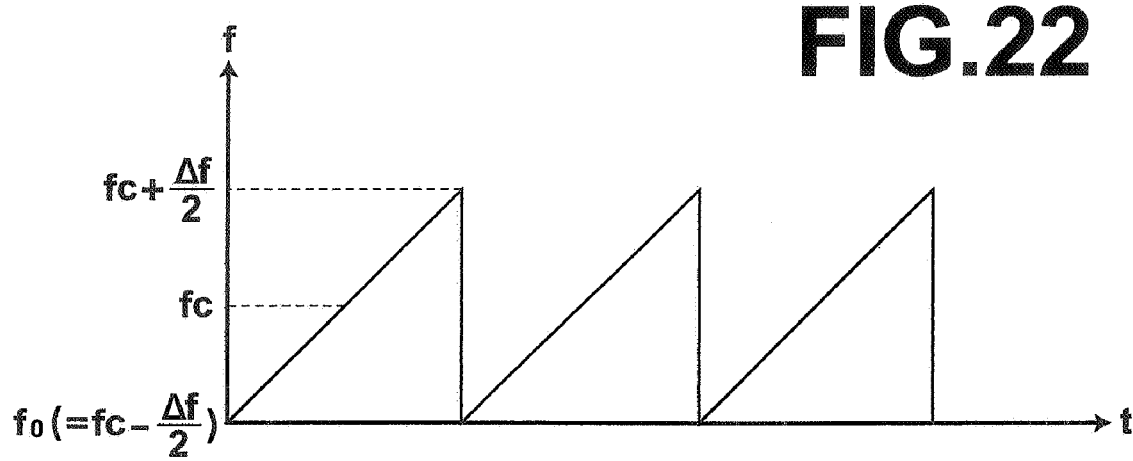
FIG. 22 is a diagram for explaining a laser beam LS.

The light source unit 610 emits the laser light beam Ls while sweeping the frequency thereof at a predetermined period. As illustrated in FIG. 22, the frequency f of the laser light beam Ls is swept within a predetermined frequency sweep width Δf having a central frequency fc. Accordingly, the frequency F is swept in a saw blade pattern within the range of a frequency$_0$ (fc−Δf/2) to (fc+Δf/2).

Note that for the sake of simplicity in description, the variation in the frequency f of the laser light beam Ls will be described. However, the frequency f=light speed c/wavelength λ. Therefore, varying the frequency f of the laser light beam Ls at a predetermined period is equivalent to varying the wavelength λ of the laser light beam Ls. The central frequency fc illustrated in FIG. 22 is the central wavelength λsc when the wavelength λ is swept at the predetermined period, and the frequency sweep width Δf is equivalent to a wavelength sweep width Δsλ. In addition, FIG. 22 illustrates an example in which the frequency is swept in a saw blade pattern. However, the frequency may be swept with any other waveform.

The central frequency fc and the frequency sweep width Δf are set such that the central wavelength λsc and the wavelength sweep width As of the laser light beam Ls satisfy the conditions:

$$\lambda sc^2/\Delta s\lambda \leq 15;$$

$$\lambda sc + (\Delta s\lambda/2) \leq 1.2 \ \mu m; \text{ and}$$

$$\lambda sc - (\Delta s\lambda/2) \geq 0.98 \ \mu m.$$

The light source unit 610 comprises: a semiconductor optical amplifier 611 (semiconductor gain medium); and an optical fiber FB70. The optical fiber FB70 is connected to both ends of the semiconductor optical amplifier 611. The semiconductor optical amplifier 611 functions to emit a slight amount of light into a first end of the optical fiber FB70, when a drive current is injected thereinto, and to amplify the light that enters it from a second end of the optical fiber FB70. When the drive current is supplied to the semiconductor optical amplifier 611, the saw blade waveform laser light La is emitted to an optical fiber FB61 from an optical oscillator formed by the semiconductor optical amplifier 611 and the optical fiber FB70.

Further, an optical divider 612 is linked to the optical fiber FB70, and a portion of the light that propagates within the optical fiber FB70 is emitted into an optical fiber FB71. Light, which is emitted from the optical finer FB71, passes through a collimating lens 613, a diffraction grating 614, and an optical system 315, to be reflected by a rotating polygon mirror 616. The light reflected by the rotating polygon mirror 616 passes through an optical system 615, the diffraction grating 614, and the collimating lens 613, to reenter the optical fiber FB71.

The rotating polygon mirror 616 rotates in the direction indicated by arrow R1, to vary the angle of each reflective surface thereof with respect to the optical axis of the optical system 615. Thereby, only a light beam having a specific frequency, from among the light spectrally split by the diffraction grating 614, is returned to the optical fiber FB71. The frequency of the light beam that reenters the optical fiber PB71 is determined by the angle formed by the optical axis of the optical system 615 and the reflective surface of the rotating polygon mirror 616. The light that reenters the optical fiber FB71 is caused to enter the optical fiber FB70 by the optical divider 612. As a result, the laser light beam Ls of the specific frequency is emitted toward the optical fiber FB61.

Accordingly, when the rotating polygon mirror 616 is rotated in the direction of arrow R1 at a constant speed, the wavelength λ of the light beam that reenters the optical fiber FB71 is varied over time, at a constant period. In this manner, the laser light beam Ls having the swept wavelengths is emitted to the optical fiber FB61 from the light source unit 610.

The light dividing means 63 is constituted by a 2×2 optical fiber coupler, for example. The light dividing means 63 functions to divide the light beam Ls, emitted by the light source unit 610 and guided through the optical fiber FB61, into a measuring light beam Ls1 and a reference light beam Ls2. The light dividing means 63 is optically connected to optical fibers FB62 and FB63. The measuring light beam Ls1 is guided through the optical fiber FB62, and the reference light beam Ls2 is guided through the optical fiber FB63. Note that the light dividing means 63 of the present embodiment also functions as the multiplexing means 64.

The optical probe 630 is to be inserted into body cavities via a forceps opening and a forceps channel, and is removably mounted to the optical fiber FB62 with an optical connector 631. The optical probe 630 comprises: a probe outer cylinder 635, which has a closed distal end; a single optical fiber 633, which is provided to extend along the axial direction of the outer cylinder 635 within the interior space thereof; a prism mirror 637, for deflecting a light beam Ls emitted from the distal end of the optical fiber 633; a rod lens 638, for condensing the light beam Ls such that it converges on the measurement target Sb, which surrounds the outer cylinder 635; and a motor 634, for rotating the prism mirror 637 with the axis of the optical fiber 633 as the rotational axis.

The optical path length adjusting means 520 is provided at the end of the optical fiber FB63 at which the reference light beam Ls2 is emitted. The optical path length adjusting means 520 functions to change the optical path length of the reference light beam Ls2, to adjust the position at which tomographic images are obtained. The optical path length adjusting means 220 comprises: a mirror 523, for reflecting the reference light beam Ls2 emitted from the optical fiber FB63; a first optical lens 521a, provided between the optical fiber FB63 and the mirror 523; and a second optical lens 521b, provided between the first optical lens 521a and the mirror 523.

The first optical lens 521a functions to collimate the reference light beam Ls2 emitted from the optical fiber FB63, and to focus the reference light beam Ls2 reflected by the mirror 523 onto the core of the optical fiber FB63. The second optical lens 521b functions to focus the reference light beam Ls2 collimated by the first optical lens 521a onto the mirror 523, and to collimate the reference light beam Ls2 reflected by the mirror 523. That is, the first optical lens 521a and the second optical lens 521b form a confocal optical system.

Accordingly, the reference light beam Ls2 emitted from the optical fiber FB63 is collimated by the first optical lens 521a, and focused on the mirror 523 by the second optical lens 521b. Thereafter, the reference light beam Ls2 reflected by the mirror 523 is collimated by the second optical lens 521b, and focused onto the core of the optical fiber FB63.

The optical path length adjusting means 520 further comprises: a base 523, on which the second optical lens 521b and the mirror 523 are fixed; and a mirror moving means 24, for moving the base 523 in the direction of the optical axis of the first optical lens 521a. The optical path length of the reference light beam Ls2 is varied, by moving the base 523 in the direction indicated by arrow A.

The multiplexing means 64 is constituted by the aforementioned 2×2 optical coupler. The multiplexing means 64 multiplexes the reference light beam Ls2, of which the frequency has been shifted and the optical path length has been adjusted by the optical path length adjusting means 520, and the reflected light beam Ls3 reflected by the measurement target Sb. The multiplexed coherent light beam Ls4 is emitted toward the coherent light detecting means 640 via the optical fiber FB64.

The coherent light detecting means 640 detects the coherent light beam Ls4, and measures the intensity thereof. The coherent light detecting means 640 comprises: InGaAs type photodetectors 642a and 642b, for measuring the intensity of the coherent light beam Ls4; and a calculating section 641, for adjusting the input balance of detection values obtained by the photodetectors 642a and 642b, to enable balanced detection. Note that the coherent light beam Ls4 is divided into two light beams by the light divided means 63, and the divided light beams are detected by the photodetectors 642a and 642b, respectively.

An image obtaining means 650 administers Fourier transform on the coherent light beam Ls4 detected by the coherent light detecting means 640 to calculate the intensity of the reflected light beam Ls3 at each depth position within the measurement target Sb. Thereby, tomographic images of the measurement target Sb are obtained. The obtained tomographic images are displayed by a display apparatus 660.

Here, detection of the coherent light beam Ls4 by the coherent light detecting means 640 and image generation by the image obtaining means 650 will be described briefly. Note that a detailed description of these two points can be found in M. Takeda, "Optical Frequency Scanning Interference Microscopes", Optical Technology Contacts, Vol. 41, No. 7, pp. 426-432, 2003.

When the measuring light beam Ls1 is irradiated onto the measurement target Sb, the reflected light beams Ls3, which are reflected at various depths within the measurement target Sb and the reference light beam Ls2 interfere with each other, with various optical path length differences. By designating the optical intensity of the interference pattern with respect to each of the optical path length differences l as S(l), the optical intensity I(k) detected by the coherent light detecting means 640 can be expressed as:

$$I(k) = \int_0^\infty S(l)[1+\cos(kl)]dl$$

wherein:
k: wave number
l: optical path length difference

The above formula may be considered as being provided as an interferogram of an optical frequency range, in which the wave number k=ω/c is a variable. For this reason, the image obtaining means 650 administers Fourier transform on the spectral interference pattern detected by the coherent light detecting means 640, to determine the optical intensity (I) of the coherent light beam Ls4. Thereby, data regarding the distance from a measuring position within the measurement target Sb and data regarding the intensity of the reflected light beam can be obtained, and generation of tomographic images is enabled.

Hereinafter, the operation of the optical tomography apparatus 600 of the above construction will be described. When obtaining a tomographic image, first, the base 523 is moved in the direction of arrow A, to adjust the optical path length such that the measurement target Sb is positioned within a measurable region. Thereafter, the light beam Ls is emitted from the light source unit 610. The light beam Ls is divided into the measuring light beam Ls1 and the reference light beam Ls2 by the light dividing means 63. The measuring light beam Ls1 is emitted within the body cavity from the optical probe 630, and irradiated on the measurement target Sb. At this time, the measuring light beam Ls1 scans the measurement target Sb one dimensionally, by the optical probe 630 operating as described above. The reflected light beam Ls3, reflected by the measurement target Sb, is multiplexed with the reference light beam Ls2, reflected by the mirror 523, to form the coherent light beam Ls4. The coherent light beam Ls4 is detected by the coherent light detecting means 640. The image obtaining means 650 administers appropriate waveform compensation and noise removal on the detected coherent light beam Ls4, then administers Fourier transform thereon, to obtain intensity distribution data of the reflected light in the depth direction of the measurement target.

Next, the motor 634 of the optical probe 630 rotates the prism mirror 637, thereby scanning the measuring light beam Ls1 on the measurement target Sb. Thereby, data regarding each portion along the scanning direction can be obtained, and a tomographic image of tomographic sections that include the scanning direction can be obtained. The tomographic image obtained in this manner is displayed by the display apparatus 660. Note that by moving the optical probe 630 in the horizontal direction in FIG. 21, the measuring light beam Ls1 can be scanned in a second direction perpendicular to the aforementioned scanning direction. Thereby, a tomographic image of tomographic sections that include the second direction can be further obtained. The tomographic image obtained in this manner is also displayed by the display apparatus 660.

The central wavelength $\lambda c$ and the wavelength sweep width $\Delta\lambda$ of the laser light beam Ls satisfy the condition:

$$\lambda c^2/\Delta\lambda \leq 15.$$

Therefore, a laser light beam having a central wavelength in the 1.0 μm band is superior to that having a central wavelength in the 1.3 μm band.

Further, the conditions:

$$\lambda c+(\Delta\lambda/2) \leq 1.2 \text{ μm}$$

$$\lambda c-(\Delta\lambda/2) \geq 0.98 \text{ μm}$$

are satisfied. Therefore, the measuring light beam Ls1 has good transmissivity with respect to the measurement target Sb, and the influence exerted on the reflected light beam Ls3 by the light absorption peaks of water at the wavelengths of 0.98 μm and 1.2 μm is decreased. Accordingly, high resolution optical tomographic images having high image quality can be obtained.

Figure 23:
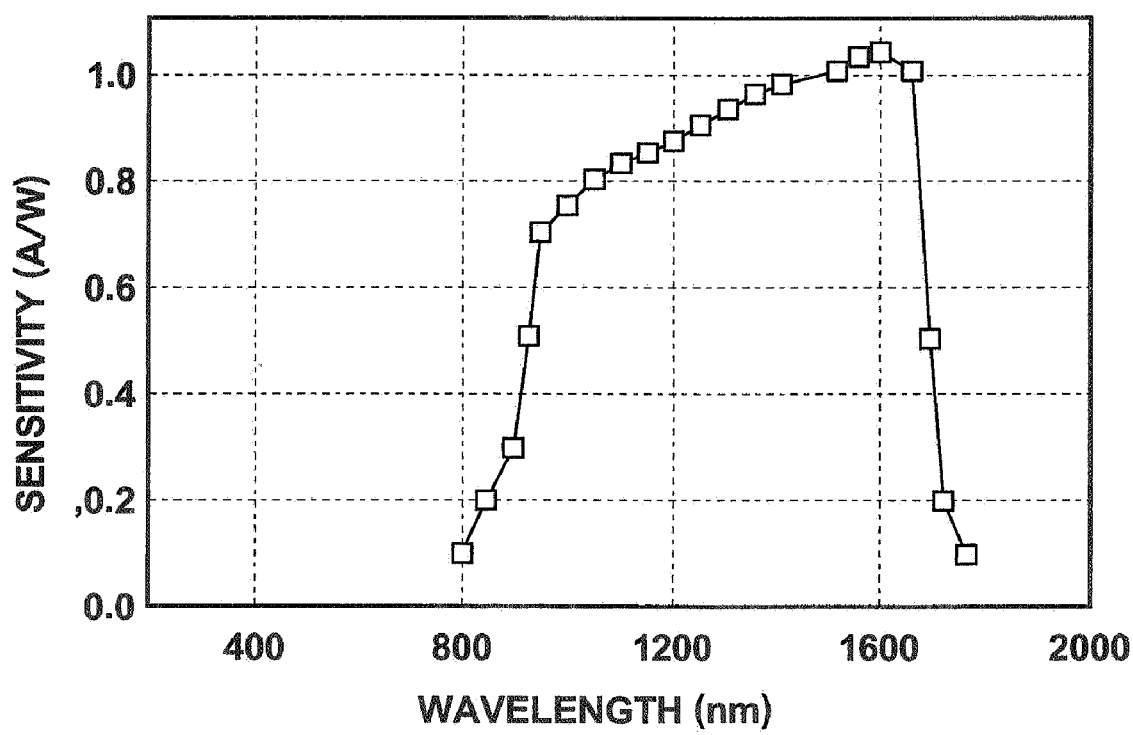
FIG. 23 is a graph that illustrates the sensitivity curve of an InGaAs type photodetector.

Note that in the case that the central wavelength $\lambda c$ of the laser light beams La is greater than or equal to 0.98 μm and less than or equal to 1.2 μm, it is preferable that InGaAs type photodetectors are employed as the photodetectors 642a and 642b, as in the present embodiment. As illustrated by the sensitivity properties illustrated in the graph of FIG. 23, InGaAs photodetectors can positively detect the coherent light beam Ls4.

Note that the optical tomography apparatus of the present invention is not limited to the embodiment described above. For example, the optical tomography apparatus 1 illustrated in FIG. 21 exemplifies a case in which the laser light beam Ls, the measuring light beam Ls1, the reference light beam Ls2, the reflected light beam Ls3, and the coherent light beam Ls4 propagate through optical fibers. Alternatively, the light beams may propagate through air or through a vacuum.

What is claimed is:

1. An optical tomography apparatus, comprising:
   a light source, for emitting a low coherence light beam;
   dividing means, for dividing the low coherence light beam into a measuring light beam and a reference light beam;
   an irradiating optical system, for irradiating the measuring light beam onto a measurement target;
   optical path length changing means, for changing the optical path length of one of the reference light beam and the measuring light beam;
   multiplexing means, for multiplexing a reflected light beam, which is the measuring light beam reflected by the measurement target, and the reference light beam, to obtain a coherent light beam; and
   image obtaining means, for detecting the intensity of the reflected light beam at a plurality of depth positions of the measurement target, at which the optical path length of the reference light beam and the sum of the optical path lengths of the measuring light beam and the reflected light beam substantially match, based on the optical intensity of the multiplexed coherent light beam, and for obtaining tomographic images of the measurement target, based on the intensities at each of the depth positions;
   a central wavelength $\lambda c$ and a full width at half maximum spectrum $\Delta\lambda$ of the reference light beam and the reflected light beam satisfying the following conditions:

$$\lambda c^2/\Delta\lambda \leq 15$$

$$\lambda c+(\Delta\lambda/2) \leq 1.2 \text{ μm}$$

$$\lambda c-(\Delta\lambda/2) \geq 0.98 \text{ μm}.$$

2. An optical tomography apparatus as defined in claim 1, wherein:
   the light source comprises a super luminescent diode.

3. An optical tomography apparatus as defined in claim 2, wherein the super luminescent diode comprises:
   a GaAs substrate having a first conductivity;
   an optical waveguide path constituted by an InGaAs active layer on the GaAs substrate; and
   a window region layer having a greater energy gap and a smaller refractive index than the active layer and a second conductivity different from the first conductivity, constituted by a binary or ternary semiconductor material with a lattice coefficient that lattice matches with GaAs within a range of ±0.1% and does not contain Al, provided at a rear emitting facet of the optical waveguide path.

4. An optical tomography apparatus as defined in claim 3, wherein:
   the semiconductor material of the window region layer is one of GaAs and InGaP.

5. An optical tomography apparatus as defined in claim 1, wherein: the light source comprises phosphor that contains near infrared fluorescent pigment.

6. An optical tomography apparatus as defined in claim 1, wherein:
   the light source comprises one of a Yb type pulse laser, an Nd type pulse laser, and a Ti type pulse laser.

7. An optical tomography apparatus as defined in claim 1, further comprising:
   a Gaussian spectrum forming filter.

8. An optical tomography apparatus, comprising:
   a light source, for emitting a low coherence light beam;
   dividing means, for dividing the low coherence light beam into a measuring light beam and a reference light beam;

an irradiating optical system, for irradiating the measuring light beam onto a measurement target;

multiplexing means, for multiplexing a reflected light beam, which is the measuring light beam reflected by the measurement target, and the reference light beam, to obtain a coherent light beam; and image obtaining means, for calculating the intensity of the reflected light beam at a plurality of depth positions of the measurement target, based on the properties of the multiplexed coherent light beam, and for obtaining tomographic images of the measurement target, based on the intensities at each of the depth positions;

a central wavelength $\lambda c$ and a full width at half maximum spectrum $\Delta\lambda$ of the reference light beam and the reflected light beam satisfying the following conditions:

$$\lambda c2/\Delta\lambda \leq 15$$

$$\lambda c+(\Delta\lambda/2) \leq 1.2 \,\mu m$$

$$\lambda c-(\Delta\lambda/2) \geq 0.98 \,\mu m.$$

9. An optical tomography apparatus as defined in claim 8, wherein:

the image obtaining means detects the intensity for each frequency of the coherent light beam; and calculates the intensity of the reflected light beam at the plurality of depth positions of the measurement target, based on the detected intensities for each frequency of the coherent light beam.

10. An optical tomography apparatus as defined in claim 8, wherein:

the light source comprises a super luminescent diode.

11. An optical tomography apparatus as defined in claim 10, wherein the super luminescent diode comprises:

a GaAs substrate having a first conductivity;

an optical waveguide path constituted by an InGaAs active layer on the GaAs substrate; and a window region layer having a greater energy gap and a smaller refractive index than the active layer and a second conductivity different from the first conductivity, constituted by a binary or ternary semiconductor material with a lattice coefficient that lattice matches with GaAs within a range of ±0.1% and does not contain Al, provided at a rear emitting facet of the optical waveguide path.

12. An optical tomography apparatus as defined in claim 11, wherein:

the semiconductor material of the window region layer is one of GaAs and InGaP.

13. An optical tomography apparatus as defined in claim 8, wherein:

the light source comprises phosphor that contains near infrared fluorescent pigment.

14. An optical tomography apparatus as defined in claim 8, wherein:

the light source comprises one of a Yb type pulse laser, an Nd type pulse laser, and a Ti type pulse laser.

15. An optical tomography apparatus as defined in claim 8, further comprising:

a Gaussian spectrum forming filter.

16. An optical tomography apparatus, comprising:

a light source, for emitting a laser beam while sweeping through wavelengths at a predetermined period;

dividing means, for dividing the laser beam into a measuring light beam and a reference light beam;

an irradiating optical system, for irradiating the measuring light beam onto a measurement target;

multiplexing means, for multiplexing a reflected light beam, which is the measuring light beam reflected by the measurement target, and the reference light beam, to obtain a coherent light beam;

coherent light detecting means, for calculating the intensity of the reflected light beam at a plurality of depth positions within the measurement target, based on the frequency and the intensity of the coherent light beam; and image obtaining means, for obtaining tomographic images of the measurement target, based on the intensities of the reflected light beam at each of the depth positions;

the central wavelength $\lambda sc$ of the sweep and the wavelength sweep width $\Delta\lambda s$ of the laser light beam satisfying the following conditions:

$$\lambda sc2/\Delta\lambda s \leq 15$$

$$\lambda sc+(\Delta\lambda s/2) \leq 1.2 \mu m$$

$$\lambda sc-(\Delta\lambda s/2) \geq 0.98 \,\mu m.$$

17. An optical tomography apparatus as defined in claim 16, wherein:

the coherent light detecting means comprises an InGaAs type photodetector.

* * * * *